US008221991B2

(12) United States Patent
Kliewer et al.

(10) Patent No.: US 8,221,991 B2
(45) Date of Patent: Jul. 17, 2012

(54) ORPHAN NUCLEAR RECEPTOR

(75) Inventors: Steven A. Kliewer, Cary, NC (US);
Stacey A. Jones, Wake Forest, NC (US);
Timothy M. Willson, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/877,195

(22) Filed: Sep. 8, 2010

(65) Prior Publication Data
US 2011/0059478 A1  Mar. 10, 2011

Related U.S. Application Data

(62) Division of application No. 11/766,871, filed on Jun. 22, 2007, now abandoned, which is a division of application No. 09/276,935, filed on Mar. 26, 1999, now Pat. No. 7,238,491.

(60) Provisional application No. 60/079,593, filed on Mar. 27, 1998.

(51) Int. Cl.
*G01N 33/53* (2006.01)
(52) U.S. Cl. ..................... 435/7.2; 435/69.1
(58) Field of Classification Search ............... None
See application file for complete search history.

(56) References Cited

U.S. PATENT DOCUMENTS

| 2003/0332709 | 2/2003 | Berkenstam et al. |
| 2003/0064430 A1 | 4/2003 | Evans et al. |

FOREIGN PATENT DOCUMENTS

| JP | 11-127872 | 5/1999 |
| WO | WO99/48915 | 9/1999 |
| WO | WO 99/48915 | 9/1999 |
| WO | WO 00/37077 | 6/2000 |
| WO | WO01/97856 A2 | 12/2001 |

OTHER PUBLICATIONS

Maurel, P., Cytochromes P450: Metabolic and Toxicological Aspects (ed.Ioannides, C.), pp. 241-270 (CRC Press, Inc., Boca Raton, FL (1996).
Guzelian, P.S., Microsomes and Drug Oxidations (eds. Miners et al), pp. 148-155 (Taylor and Francis, London (1988).
Hashimoto et al., Gene structure of CYP3A5, an adult-specific form of cytochrome P450 in human livers and its transcriptional control, Eur. J. Biochem, 218:585-595 (1993).
Barwick et al., Trans-species Gene Transfer for Analysis of Glucocorticoid-Inducible Transcriptional Activation of Transiently Expressed Human CYP3A4 and Rabbit CYP3A6 in Primary Cultures of Adult Rat and Rabbit Hepatocytes, Molec. Pharmacol 50:10-16 (1996).
Fields et al., A novel gnetic system to detect protein-protein interactions, Nature 340:245-246 (1989).
Forman et al., Hypolipidemic drugs, polyunsaturated fatty acids and eicosanoids are ligands for peroxisome proliferator-activated receptors α and σ, Proc. Natl. Acad. Sci. USA 94:4312-4317 (1997).
Luckow et al., CAT constructions with multiple unique restriction sites for the functional analysis of eukaryotic promoters and regulatory elements, Nucleic Acids Research 15(13):5490-(1987).
Kliewer et al., An Orphan Nuclear Receptor Activated by Pregnanes Defines a Novel Steroid Signaling Pathway, Cell 92:73-82 (1998).
Smith et al., A novel nuclear receptor superfamily member in Xenopus that associateds with RXR and shares extensive sequence similarity to the mammalian vitamin D3 receptor, Nucleic Acids Research 22(1):66-71 (1994).
Nagpal et al, RAR-β4, a retinoic acid receptor isoform is generated from RAR-β2 by alternative splicing and usage of a CUG initiator codon, Proc. Natl., Acad., Sci. USA 89:2718-2722 (1992).
Quattrochi et al, A Novel cisActing Element in a Liver Cytochrome P450 3A Gene Confers Synergistic Induction by Glucocorticoids plus Antiglucocorticoids, The Journal of Biological Chemistry 270(48); 28917-28923 (1995).
Huss et al. Dexamethasone responsiveness of a major glucocorticoid-inducible CYP3A gene is mediated by elements unrelated to a glucocortincoid receptor binding motif, Proc. Natl. Acad. Sci USA 93: 4666-4670 (1996).
Molowa et al., Complete cDNA sequence of a cytochrome P-450 inducible by glucocoritcoids in human liver, Proc. Natl. Acad. Sci. USA 83:5311-5315 (1986).
Kocarek et al., Comparative Analysis of Cytochrome P4503A Induction in Primary Cultures of Rat, Rabbit and Human Hepatocytes, Drug Metabolism and Disposition 23(3): 415-421 (1995).
Schuetz et al, Induction of Cytochrome P-450 by Glucocorticoids in Rat Liver, The Journal of Biological Chemistry 259(3):2007-2012 (1984).
Heuman et al., Immunochemical Evidence for Induction of a Common form of Hepatic Cytochrome P-450 in Rats Treated with Pregnenolone-16α carbonitrile or other Steroidal or Non-Steroidal Agents, Molecular Pharmacology 21:753-760 (1982).
Schulte-Hermann et al, Quantitative Structure-Activity Studies on Effects of Sixteen Different Steroids on Growth and Monoxygenases of Rat Liver, Cancer Research 48:2462-2468 (1988).
Wrighton et al, Identification of the Cytochrom P-450 Induced by Macrolide Antibiotics in Rat Liver as the Glucocorticoid Responsive Dytochrome P-450, Biochemistry 24:2171-2178 (1985).
Hostetler et al, Coinduction of Multiple Hepatic Cytochrome P-450 Proteins and Their MrNAs in Rats Treated with Imidazole Antimycotic Agents, Molecular Phamacology 35:279-285 (1989).
Kocarek et al, Regulation of Phenobarbital-Inducible Cytochrom P450 2B1/2 mRNA by Lovastatin and Oxysterols in Primay Cultures, Toxicology and Applied Pharmacology 120:298-308 (1993).
Schuetz et al, Regulation of Human Liver Cytochromes P-450 in family 3A in Primary Continuous Culture of Human Hepatocytes, Hepatology 18:1254-1262 (1993).

(Continued)

*Primary Examiner* — Michael Pak
(74) *Attorney, Agent, or Firm* — Michael M. Conger

(57) ABSTRACT

The present invention relates to a novel human orphan nuclear receptor that binds to a cytochrome P-450 monooxygenase (CYP) promoter and that is activated by compounds that induce CYP gene expression. The invention further relates to nucleic acid sequences encoding such a receptor, to methods of making the receptor and to methods of using the receptor and nucleic acid sequences encoding same. The invention also relates to non-human animals transformed to express the human receptor and to methods of using such animals to screen compounds for drug interactions and toxicities.

1 Claim, 12 Drawing Sheets

OTHER PUBLICATIONS

Calleja et al., The antibiotic rifampicin is a nonsteroidal ligand and activator of the human glucocorticoid receptor, Nature Medicine 4(1):92-96 (1998).

Krey et al., Fatty Acids, Eicosanoids and hypolipidemic Agents Identified as Ligands of Peroxisome Proliferator-Activated Receptors by Coactivator-Dependent Receptor Ligand Assay, Molecular Endocrinology 11:779-791 (1997).

Kliewer et al., Transcriptional Regulation of Energy Balance by the PPARs, 9th International CBT Symposium on Nuclear Steroid and Orphan Receptors, Oral Presentation, Oct. 12-15, 1997, Huddinge, Sweden.

Blumberg et al, BXR an embryonic orphan nuclear receptor activated by a novel class of endogenous benzoate metabolites, Genes & Development 12:12691-1277 (1998).

Lehmann et al., The Human Orphan Nuclear Receptor PXAR is Activated by Compounds that Regulate CYP3A4 Gene Expression and Cause Drug Interactions, J. Clin. Invest. 102(5):1016-1023 (1998).

Blumbert et al., SXR a novel steroid and xenobiotic-sensing nuclear receptor, Genes & Development 12:3195-3205 (1998).

Jones et al., The Pregnane X Receptor a Promiscuous Xenobiotic Receptor that has Diverged during Evolution, Molecular Endocrinology 14(1):27-39 (2000).

Bowie et al., (1990) Science 247:1307-1310.

Paolini Moreno et al, Mechanism for the prevention of cholestasis involving cytochrom P4503A overexpression, Journal of Investigative Medicine, 48(1):49-50 (Jan. 2000-01).

Paolini Moreno et al., Bile acid structure and selective modulation of murine hepatic cytochrome P450-lined enzymes, Hepatology 30(3):730-739 (1999).

Moore Linda et al., St. John's wort induced hepatic drug metabolism through activation of the pregnane X receptor, Proceedings of the National Academy of Sciences of the United States, 97(13):7500-7502 (Jun. 20, 2000).

A

```
   1 TGAAATATAGGTGAGAGACAAGATTGTCTCATATCCGGGGAAATCATAACCTATGACTAG
  61 GACGGGAAGAGGAAGCACTGCCTTTACTTCAGTGGGAATCTCGGCCTCAGCCTGCAAGCC
 121 AAGTGTTCACAGTGAGAAAAGCAAGAGAATAAGCTAATACTCCTGTCCTGAACAAGGCAG
 181 CGGCTCCTTGGTAAAGCTACTCCTTGATCGATCCTTTGCACCGGATTGTTCAAAGTGGAC
 241 CCCAGGGGAGAAGTCGGAGCAAAGAACTTACCACCAAGCAGTCCAAGAGGCCCAGAAGCA
 301 AACCTGGAGGTGAGACCCAAAGAAAGCTGGAACCATGCTGACTTTGTACACTGTGAGGAC
            L   E   V   R   P   K   E   S   W   N   H   A   D   F   V   H   C   E   D  19
 361 ACAGAGTCTGTTCCTGGAAAGCCCAGTGTCAACGCAGATGAGGAAGTCGGAGGTCCCCAA
        T   E   S   V   P   G   K   P   S   V   N   A   D   E   E   V   G   G   P   Q  39
 421 ATCTGCCGTGTATGTGGGGACAAGGCCACTGGCTATCACTTCAATGTCATGACATGTGAA
        I   C   R   V   C   G   D   K   A   T   G   Y   H   F   N   V   M   T   C   E  59
 481 GGATGCAAGGGCTTTTTCAGGAGGGCCATGAAACGCAACGCCCGGCTGAGGTGCCCCTTC
        G   C   K   G   F   F   R   R   A   M   K   R   N   A   R   L   R   C   P   F  79
 541 CGGAAGGGCGCCTGCGAGATCACCCGGAAGACCCGGCGACAGTGCCAGGCCTGCCGCCTG
        R   K   G   A   C   E   I   T   R   K   T   R   R   Q   C   Q   A   C   R   L  99
 601 CGCAAGTGCCTGGAGAGCGGCATGAAGAAGGAGATGATCATGTCCGACGAGGCCGTGGAG
        R   K   C   L   E   S   G   M   K   K   E   M   I   M   S   D   E   A   V   E  119
 661 GAGAGGCGGGCCTTGATCAAGCGGAAGAAAAGTGAACGGACAGGGACTCAGCCACTGGGA
        E   R   R   A   L   I   K   R   K   K   S   E   R   T   G   T   Q   P   L   G  139
 721 GTGCAGGGGCTGACAGAGGAGCAGCGGATGATGATCAGGGAGCTGATGGACGCTCAGATG
        V   Q   G   L   T   E   E   Q   R   M   M   I   R   E   L   M   D   A   Q   M  159
 781 AAAACCTTTGACACTACCTTCTCCCATTTCAAGAATTTCCGGCTGCCAGGGGTGCTTAGC
        K   T   F   D   T   T   F   S   H   F   K   N   F   R   L   P   G   V   L   S  179
 841 AGTGGCTGCGAGTTGCCAGAGTCTCTGCAGGCCCCCATCGAGGGAAGAAGCTGCCAAGTGG
        S   G   C   E   L   P   E   S   L   Q   A   P   S   R   E   E   A   A   K   W  199
 901 AGCCAGGTCCGGAAAGATCTGTGCTCTTTGAAGGTCTCTCTGCAGCTGCGGGGGGAGGAT
        S   Q   V   R   K   D   L   C   S   L   K   V   S   L   Q   L   R   G   E   D  219
 961 GGCAGTGTCTGGAACTACAAACCCCCAGCCGACAGTGGCGGGAAAGAGATCTTCTCCCTG
        G   S   V   W   N   Y   K   P   P   A   D   S   G   G   K   E   I   F   S   L  239
1021 CTGCCCCACATGGCTGACATGTCAACCTACATGTTCAAAGGCATCATCAGCTTTGCCAAA
        L   P   H   M   A   D   M   S   T   Y   M   F   K   G   I   I   S   F   A   K  259
1081 GTCATCTCCTACTTCAGGGACTTGCCCATCGAGGACCAGATCTCCCTGCTGAAGGGGGCC
        V   I   S   Y   F   R   D   L   P   I   E   D   Q   I   S   L   L   K   G   A  279
1141 GCTTTCGAGCTGTGTCAACTGAGATTCAACACAGTGTTCAACGCGGAGACTGGAACCTGG
        A   F   E   L   C   Q   L   R   F   N   T   V   F   N   A   E   T   G   T   W  299
1201 GAGTGTGGCCGGCTGTCCTACTGCTTGGAAGACACTGCAGGTGGCTTCCAGCAACTTCTA
        E   C   G   R   L   S   Y   C   L   E   D   T   A   G   G   F   Q   Q   L   L  319
1261 CTGGAGCCCATGCTGAAATTCCACTACATGCTGAAGAAGCTGCAGCTGCATGAGGAGGAG
        L   E   P   M   L   K   F   H   Y   M   L   K   K   L   Q   L   H   E   E   E  339
1321 TATGTGCTGATGCAGGCCATCTCCCTCTTCTCCCCAGACCGCCCAGGTGTGCTGCAGCAC
        Y   V   L   M   Q   A   I   S   L   F   S   P   D   R   P   G   V   L   Q   H  359
1381 CGCGTGGTGGACCAGCTGCAGGAGCAATTCGCCATTACTCTGAAGTCCTACATTGAATGC
        R   V   V   D   Q   L   Q   E   Q   F   A   I   T   L   K   S   Y   I   E   C  379
1441 AATCGGCCCCAGCCTGCTCATAGGTTCTTGTTCCTGAAGATCATGGCTATGCTCACCGAG
        N   R   P   Q   P   A   H   R   F   L   F   L   K   I   M   A   M   L   T   E  399
1501 CTCCGCAGCATCAATGCTCAGCACACCCAGCGGCTGCTGCGCATCCAGGACATACACCCC
        L   R   S   I   N   A   Q   H   T   Q   R   L   L   R   I   Q   D   I   H   P  419
1561 TTTGCTACGCCCCTCATGCAGGAGTTGTTCGGCATCACAGGTAGCTGAGCGGCTGCCCTT
        F   A   T   P   L   M   Q   E   L   F   G   I   T   G   S   *              434
1621 GGGTGACACCTCCGAGAGGCAGCCAGACCCAGAGCCCTCTGAGCCGCCACTCCCGGGCCA
1681 AGACAGATGGACACTGCCAAGAGCCGACAATGCCCTGCTGGCCTGTCTCCCTAGGGAATT
1741 CCTGCTATGACAGCTGGCTAGCATTCCTCAGGAAGGACATGGGTGCCCCCCACCCCCAGT
1801 TCAGTCTGTAGGGAGTGAAGCCACAGACTCTTACGTGGAGAGTGCACTGACCTGTAGGTC
1861 AGGACCATCAGAGAGGCAAGGTTGCCCTTTCCTTTTAAAAGGCCCTGTGGTCTGGGGAGA
1921 AATCCCTCAGATCCCACTAAAGTGTCAAGGTGTGGAAGGGACCAAGCGACCAAGGATAGG
1981 CCATCTGGGGTCTATGCCCACATACCCACGTTTGTTCGCTTCCTGAGTCTTTTCATTGCT
2041 ACCTCTAATAGTCCTGTCTCCCACTTCCCACTCGTTCCCCTCCTCTTCCGAGCTGCTTTG
2101 TGGGCTCCAGGCCTGTACTCATCGGCAGGTGCATGAGTATCTGTGG
```

```
CYP3A4 IR6      ata TGAACT caaagg AGGTCA gtg
                    <-----        ----->

CYP3A4 IR6 m1   ata TGTTCT caaagg AGAACA gtg
                    <-xx--        --xx->

CYP3A4 IR6 m2   ata ACAACT caaagg AGGTCA gtg
                    xx----        ----->

CYP3A1 DR3      aga TGAACT tca TGAACT gtc
                    <-----     <-----
```

C

The Preparation of [³H]GW-485801

1. REACTION SCHEME

[³H]GW-485801

Kd = 370 nM

ORPHAN NUCLEAR RECEPTOR

This application is a divisional of U.S. patent application Ser. No. 11/766,871 filed Jun. 22, 2007, now abandoned which is a divisional of U.S. patent application Ser. No. 09/276,935 filed Mar. 26, 1999 (U.S. Pat. No. 7,238,491), which claims priority from Provisional Application No. 60/079,593, filed Mar. 27, 1998, each of which are incorporated herein by reference.

TECHNICAL FIELD

The present invention relates to a novel human orphan nuclear receptor that binds to a cytochrome P-450 monooxygenase (CYP) promoter and that is activated by compounds that induce CYP gene expression. The invention further relates to nucleic acid sequences encoding such a receptor, to methods of making the receptor and to methods of using the receptor and nucleic acid sequences encoding same. The invention also relates to non-human animals transformed to express the human receptor and to methods of using such animals to screen compounds for drug interactions and toxicities.

BACKGROUND OF THE INVENTION

Members of the cytochrome P-450 (CYP) family of hemoproteins are critical in the oxidative metabolism of a wide variety of endogenous substances and xenobiotics, including various carcinogens and toxins (Nebert et al, Ann. Rev. Biochem. 56:945-993 (1987)). In man, the CYP3A4 monooxygenase plays a major role in the biotransformation of drugs due to its abundance in liver and intestine and its broad substrate specificity. CYP3A4 catalyzes the metabolism of >60% of all drugs that are in use including steroids, immunosuppressive agents, imidazole antimycotics, and macrolide antibiotics (Maurel, P. in Cytochromes P450: metabolic and toxicological aspects (ed. Ioannides, C.) 241-270 (CRC Press, Inc., Boca Raton, Fla., 1996).

Expression of the CYP3A4 gene is markedly induced both in vivo and in primary hepatocytes in response to treatment with a variety of compounds. Many of the most efficacious inducers of CYP3A4 expression are commonly used drugs such as the glucocorticoid dexamethasone, the antibiotic rifampicin, the antimycotic clotrimazole, and the hypocholesterolemic agent lovastatin (Maurel, P. in Cytochromes P450: metabolic and toxicological aspects (ed. Ioannides, C.) 241-270 (CRC Press, Inc., Boca Raton, Fla., 1996), Guzelian, P. S. in Microsomes and Drug Oxidations (eds. Miners, J. O., Birkett, D. J., Drew, R. & McManus, M.) 148-155 (Taylor and Francis, London, 1988). The inducibility of CYP3A4 expression levels coupled with the broad substrate specificity of the CYP3A4 protein represent the basis for many drug interactions in patients undergoing combination drug therapy. While attempts have been made to develop in vivo and in vitro assays with which to profile the effects of compounds on CYP3A expression levels, these efforts have been hampered by species-specific effects that have limited the utility of using animals and their tissues for testing purposes. Thus, analysis of the effects of new compounds on CYP3A4 gene expression has been largely restricted to laborious assays involving human liver tissue.

Recently, efforts have been directed at understanding the molecular basis for the induction of CYP3A4 gene expression. The CYP3A4 promoter has been cloned and a 20 bp region residing approximately 150 bp upstream of the transcription initiation site shown to confer responsiveness to dexamethasone and rifampicin (Hashimoto et al, Eur. J. Biochem. 218:585-595 (1993), Barwick et al, Molec. Pharmacol. 50:10-16 (1996)). This region contains two copies of the AG(G/T)TCA motif recognized by members of the nuclear receptor superfamily, suggesting that a nuclear receptor might be responsible for mediating at least some of the effects of the chemical inducers of CYP3A4 expression. However, prior to the present invention, proteins that bind to this response element had not been characterized.

The present invention is based on the identification of a novel orphan nuclear receptor that binds to a response element in the CYP3A4 promoter and that is activated by a range of compounds known to induce CYP3A4 expression. The identification of this receptor makes possible assays that can be used to establish whether drugs will interact in vivo.

SUMMARY OF THE INVENTION

The present invention relates to a novel human orphan nuclear receptor, designated the human pregnane X receptor (hPXR), that binds to a CYP promoter, for example, the rifampicin/dexamethasone response element in the cytochrome P-450 monooxygenase 3A4 (CYP3A4) promoter. The receptor is activated to modulate transcription of a CYP (e.g., CYP3A4) gene. The present invention further relates to nucleic acids encoding hPXR, including expression vectors that can be used to effect expression of the receptor in host cells. The invention also relates to host cells transformed with such expression vectors and to methods of using the receptor and receptor encoding sequences in assays designed to screen compounds (e.g., drugs) for their ability to modulate CYP (e.g., CYP3A4) gene expression. The invention also relates to non-human animals transformed to express the human receptor and to methods of using same in drug screens.

BRIEF DESCRIPTION OF THE DRAWINGS

FIGS. 1A-1D. Molecular cloning of hPXR. (FIG. 1 A) Nucleotide (SEQ ID NO:13) and predicted amino acid (SEQ ID NO:14) sequences of hPXR. (FIG. 1B) Amino acid sequence comparison between hPXR, mPXR1, Xenopus orphan nuclear receptor 1 (xONR1) (Smith et al, Nucl. Acids Res. 22:66-71 (1994)), and the human vitamin D receptor (hVDR). Numbers indicate percent amino acid identity in the DBDs and LBDs. (FIG. 1C) The hPXR clone encodes a functional nuclear receptor. Transfection assays were performed with a pSG5-hPXR expression vector containing the wild-type 5' region of the hPXR cDNA and a reporter plasmid containing four copies of the CYP3A1 DR3 PXRE. Cells were treated with vehicle alone (0.1% DMSO) or 10 µM of dexamethasone-t-butylacetate. Cell extracts were subsequently assayed for CAT activity. Data points represent the mean of assays performed in duplicate. (FIG. 1D) Translation of the full-length hPXR initiates at a non-AUG codon. In vitro transcription and translation were performed with the pSG5-hPXR expression vector containing the wild-type 5' region to of the hPXR cDNA or pSG5-hPXR AUG, in which the CUG codon at nucleotide positions 304-306 was modified to AUG. The 50 kD product synthesized when either template was used is indicated by the open arrow and the asterisk. Two shorter products which are likely to represent translation initiation at methionine-56 and methionine-69 within the DBD are indicated by closed arrows. A longer translation product present at low levels is indicated by the bent arrow. Size markers (in kD) are indicated at left.

(FIG. 3A) CV-1 cells were cotransfected with the $(IR6)_3$-tk-CAT reporter plasmid in either the absence (−) or presence (+) of the pSG5-hPXR ATG expression plasmid and treated with vehicle alone (open bars) or 10 μM dexamethasone-t-butylacetate (closed bars). Cell extracts were subsequently assayed for CAT activity. Data represent the mean of assays performed in triplicate +/−S.E. (FIG. 3B) Oligonucleotides used in band shift assays. The positions of nuclear receptor half-site motifs and mutations are indicated. (FIG. 3C) Band shift assays were performed with a radiolabeled oligonucleotide containing the CYP3A4 IR6 PXRE and hRXR and either hPXR (top panel) or mPXR1 (bottom panel). Unlabeled competitor oligonucleotides were added at a 10-fold or 50-fold molar excess as indicated.

(FIG. 4A) CV-1 cells were transfected with the pSG5-hPXR ATG or pSG5-mPXR1 expression plasmids and the $(IR6)_3$-tk-CAT reporter (left and middle panels, respectively), or the RS-hGR expression plasmid (Giguere et al, Cell 46:645-652 (1986)) and a reporter containing two copies of a consensus glucocorticoid response element upstream of tk-CAT (right panel). Cells were treated with 1 μM mevastatin or lovastatin, 100 μM phenobarbital, or 10 μM of the other compounds. Cell extracts were subsequently assayed for CAT activity. Data represent the mean of assays performed in triplicate +/−S.E. (FIG. 4B) Structures of representative compounds that activate hPXR. (FIG. 4C) CARLA was performed with bacterially-expressed GST-hPXR or GST-mPXR1 and [$^{35}$S]SRC1.14 synthesized in vitro. [$^{35}$S]SRC1.14 was mixed with either GST-hPXR or GST-mPXR1 in the presence of vehicle alone (1) (1% DMSO) or 10 μM of dexamethasone-t-butylacetate (2), rifampicin (3), or clotrimazole (4). [$^{35}$S]SRC1.14 complexed with GST-hPXR (top panel) or GST-mPXR1 (bottom panel) was precipitated with glutathione-sepharose beads.

DETAILED DESCRIPTION OF THE INVENTION

Figure 1B:
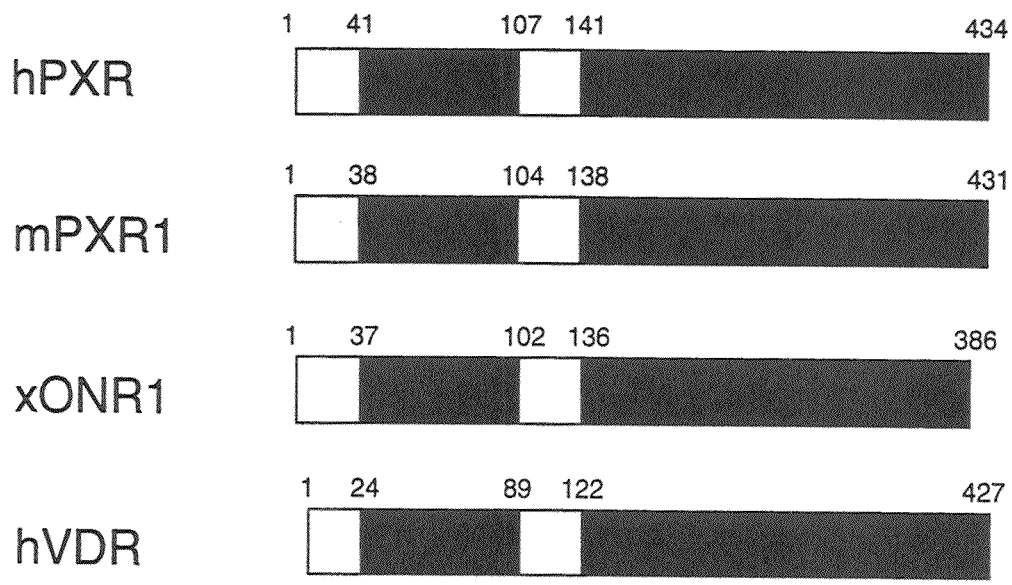

The present invention relates to a novel human nuclear receptor, hPXR. The invention further relates to nucleic acid sequences encoding hPXR, to constructs comprising such sequences, to host cells containing the constructs and to a method of producing hPXR using such host cells. The invention also relates to non-human animals transformed to express hPXR. The invention further relates to in vivo and in vitro assays that can be used to identify compounds that induce CYP expression. While the disclosure that follows makes specific reference to CYP3A4, it should be appreciated that the details (e.g., methods) provided find application in connection with other CYP genes as well.

hPXR is characterized as a protein comprising about 43.4 amino acids and having a molecular weight of about 49.7 kilodaltons. hPXR binds to a DNA response element in the CYP3A4 promoter as a heterodimer with the 9-cis retinoic acid receptor, RXR. hPXR is activated by compounds known to modulate CYP3A4 expression. The receptor is most abundantly expressed in liver but is also present in colon and small intestine.

One embodiment of the receptor of the invention has the amino acid sequence set forth in FIG. 1, or an analog thereof (wherein the term analog is intended to indicate a naturally occurring human variant of the FIG. 1 sequence), or a fragment thereof, including fragments having at least one functional characteristic of hPXR (e.g., ligand binding or DNA binding). Preferred fragments include portions of the FIG. 1 sequence at least 30 consecutive amino acids in length, more preferably, at least 50 consecutive amino acids in length, and most preferably, at least 75 consecutive amino acids in length. Specific fragments include the ligand binding domain (that is, amino acids 141 to 434 of the FIG. 1 sequence) and the DNA binding domain (that is amino acids 41 to 107 of the FIG. 1 sequence) as well as the domain that is used for the ligand binding assay described in the Examples that follow (that is, amino acids 130-434 of the FIG. 1 sequence). The invention also includes a protein comprising a domain sharing at least 80% amino acid sequence identity with the ligand binding domain of the FIG. 1 sequence, more preferably, at least 85% amino acid sequence identity and, most preferably, at least 90% or 95%, 96%, 97%, 98% or 99% amino acid sequence identity with the ligand binding domain of the FIG. 1 sequence (% sequence identity being determined, for example, by Basic Blast (version 2.0) available through the NCBI website http://www.ncbi.nlm.nih.gov/), and, advantageously, retaining the function of the FIG. 1 sequence.

The receptor of the invention, or fragment thereof, can bear a detectable label (e.g., a radioactive or fluorescent label). The receptor, or receptor fragment, can also be bound to a solid support, e.g., a glass or plastic particle, a plate, or a filter.

Nucleic acid sequences of the invention include DNA and RNA sequences encoding hPXR, for example, hPXR having the amino acid sequence given in FIG. 1, as well as nucleic acid sequences encoding analogs and fragments of the FIG. 1 amino acid sequence as defined above, and nucleic acid sequences encoding proteins comprising a domain sharing at least 80% amino acid sequence identify (more preferably, at least 8.5%, or at least 90%, or at least 95%, or at least 96%, or at least 97%, or at least 98% or at least 99%) with the ligand binding domain of the FIG. 1 sequence, as described above. A specific nucleic acid sequence of the invention is that shown in FIG. 1.

The hPXR encoding sequence can be present in a construct, for example, in an expression construct, operably linked to 4 promoter (e.g., the CMV, SV40, Taq, T7 or LacO promoter). Such expression constructs are operative in a cell in culture (e.g., yeast, bacteria, insect or mammalian), to express the encoded hPXR, or fragment thereof. Preferred expression vectors include pGEX, pET, pFASTbacHT and pSG5.

The invention also relates to cells in culture (e.g., yeast, bacteria or mammalian (for example, CV-1, HuH7, HepG2, or CaCo2 cells)) that are transformed with an above-described construct. Transformation can be effected using any of a variety of standard techniques. Such cells can be used in a method of making hPXR (or fragment thereof) by culturing same under conditions suitable for expression of the polypeptide product.

The invention further relates to chimeric receptors (or fusion proteins having a receptor component) (and encoding sequences) comprising at least a DNA-binding domain or a ligand-binding domain of hPXR, and a non-hPXR derived sequence. Non-hPXR derived sequences can be selected so as to be suitable for the purpose to be served by the chimeric receptor. Examples of such sequences include glutathione-S-transferase and the DNA binding domain of yeast transcription factor GAL4 and other DNA binding domains, e.g., DNA binding domains for the estrogen and glucocorticoid receptors. The chimeric receptor can bear a detectable label (e.g., a radioactive or fluorescent label). The chimeric receptor can also be bound to a solid support, e.g., a glass or plastic particle, a plate or a filter.

A further aspect of the invention relates to in vitro (cell-free) and in vivo (cell-based) assays that can be used to profile the effects of compounds (e.g. potential new drugs) on CYP3A4 levels. The inducibility of CYP3A4 levels, coupled with the broad substrate specificity of the CYP3A4 enzyme, represent the basis for many drug-drug interactions in patients undergoing multiple drug therapy. Ideally, new drugs would have little or no effect on CYP3A4 expression levels.

The assays of the invention can take any of a variety of forms. As compounds that activate hPXR function as inducers of CYP3A4 gene expression, hPXR binding and activation assays provide efficient means to identify compounds that can be expected to activate CYP3A4.

Binding assays of the invention include cell free assays in which hPXR, or the ligand binding domain thereof (alone or present as a fusion protein), is incubated with a test compound which, advantageously, bears a detectable label (e.g., a radioactive or fluorescent label). The hPXR, or ligand binding domain thereof, free or bound to test compound, is then separated from free test compound using any of a variety of techniques (e.g., using gel filtration chromatography (for example, on Sephadex G50 spin columns) or through capture on a hydroxyapatite resin). The amount of test compound bound to hPXR or ligand binding domain thereof, is then determined (for example, by liquid scintillation counting in the case of radiolabelled test compounds).

An alternative approach for detecting radiolabeled test compound bound to hPXR, or ligand binding domain thereof, is a scintillation proximity assay (SPA). In this assay, a bead (or other particle) is impregnated with scintillant and coated with a molecule that can capture the hPXR, or ligand binding domain thereof (e.g., streptavidin-coated beads can be used to capture biotinylated hPXR ligand binding domain). Radioactive counts are detected only when the complex of radiolabeled test compound and the hPXR, or ligand binding domain thereof, is captured on the surface of the SPA bead, bringing the radioactive label into sufficient proximity to the scintillant to emit a signal. This approach has the advantage of not requiring the separation of free test compound from bound (Nichols et al, Anal. Biochem. 257:112-119 (1998)).

Assays to determine whether a test compound interacts with the hPXR ligand binding domain can also be performed via a competition binding assay. In this assay, hPXR, or ligand binding domain thereof, is incubated with a compound known to interact with hPXR, which compound, advantageously, bears a detectable label (e.g., a radioactive or fluorescent label (see Example 5—Crabtree catalysts suitable for use in the synthetic approach described in'Example 5 include those reported by Chen et al, J. Labelled Compd. Radiopharm. 39:291 (1997) and Crabtree et al, Inorg. Synth. 28:56 (1990))). A test compound is added to the reaction and assayed for its ability to compete with the labeled compound for binding to hPXR, or ligand binding domain thereof. A standard assay format employing a step to separate free known (labeled) compound from bound, or an SPA format, can be used to assess the ability of the test compound to compete.

A further example of a binding assay in accordance with the invention is based on the finding that hPXR ligands induce the interaction of hPXR ligand binding domain with coactivators (e.g., SRC1, TIF-1, TIF-2 or ACTR, or fragment thereof). To determine if a test compound activates hPXR, and thus induces CYP3A4 expression, the ligand binding domain of hPXR is prepared (e.g., expressed) as a fusion protein (e.g., with glutathione-S-transferase (GST), a histidine tag or a maltose binding protein). The fusion protein and coactivator (either or both advantageously labeled with a detectable label, e.g., a radiolabel or fluorescent tag) are incubated in the presence and absence of the test compound and the extent of binding of the coactivator to the fusion protein determined. The induction of interaction in the presence of the test compound is indicative of an hPXR activator.

hPXR activation assays in accordance with the invention can be carried out using full length hPXR and a reporter system comprising one or more copies of the DNA binding site recognized by the hPXR binding domain (see Example 3). Advantageously, however, the activation assays are conducted using established chimeric receptor systems. For example, the ligand binding domain of hPXR can be fused to the DNA binding domain of, for example, yeast transcription factor GAL4, or that of the estrogen or glucocorticoid receptor. An expression vector for the chimera (e.g., the GAL4-hPXR chimera) can be transfected into host cells (e.g., CV-1, HuH7, HepG2 or CaCo2 cells) together with a reporter construct. The reporter construct can comprise one or more (e.g., 5) copies of the DNA binding site recognized by the binding domain present in the chimera (e.g., the GAL4 DNA binding site) driving expression of a reporter gene (e.g., CAT, SPAP or luciferase). Cells containing the constructs are then treated with either vehicle alone or vehicle containing test compound, and the level of expression of the reporter gene determined. In accordance with this assay, enhancement of expression of the reporter gene in the presence of the test compound indicates that the test compound activates hPXR and thus can function as an inducer of CYP3A4 gene expression. (See Example 4.)

Another format suitable for use in connection with the present invention is the yeast two-hybrid assay. This is an established approach to detect protein-protein interactions that is performed in yeast. Protein #1, representing the bait, is expressed in yeast as a chimera with a DNA binding domain (e.g., GAL4). Protein #2, representing the predator, is expressed in the same yeast cell as a chimera with a strong transcriptional activation domain. The interaction of bait and predator results in the activation of a reporter gene (e.g., luciferase or β-galactosidase) or the regulation of a selectable marker (e.g., LEU2 gene). This approach can be used as a screen to detect, for example, ligand-dependent interactions between hPXR1 and other proteins such as coactivator proteins (e.g., SRC1, TIF1, TIF2, ACTR) or fragments thereof. (Fields et al, Nature 340:245-246 (1989)).

Still another format is the ligand-induced complex formation (LIC) assay. This is an approach to detect ligand-mediated effects on nuclear receptor-DNA interactions. hPXR (or, minimally, the DNA and ligand binding domains thereof) can be incubated with its heterodimeric partner RXR in the presence of DNA representing, an established hPXR/RXR binding site. Test compounds can be assayed for their ability to either enhance or interfere with binding of the hPXR/RXR heterodimer to DNA (Forman et al, Proc. Natl. Acad. Sci. USA 94:4312-4317 (1997)).

Compounds that bind PXR with a suitable pKi, for example with a pKi>5, can be screened for selectivity for PXR versus other nuclear receptors (e.g., RXR) using standard binding assays. A compound that binds selectively to PXR (that is, has at least a 10 fold greater affinity for PXR, preferably, at least a 100 fold greater affinity for 25, PXR, than, for example, the glucocorticoid receptor) and thereby affects the functional activity of PXR in a cell (e.g., a cell in culture, a cell present in a tissue or a cell present in a whole animal) can be used to associate PXR activity with a mammalian disease state. For example, a compound that activates PXR induces CYP3A. Thus, diseases in which CYP3A activity is important are associated with PXR, and compounds that activate or deactivate PXR may be useful in prevention or treatment of such diseases. By using the associating methods of this invention, new PXR-associated diseases can be discovered. Once these new associations are discovered, new drugs for these diseases can be identified by screening for compounds that activate or deactivate PXR.

An example of a compound suitable for use in making disease associations in accordance with the method described above is the compound of formula I:

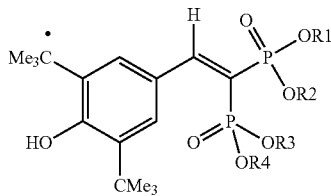

wherein each of R1, R2, R3 and R4 is, independently, $C_1$-$C_6$alkyl (linear or branched), preferably, $C_2$ or $C_3$alkyl (e.g., ethyl, n-propyl or iso-propyl), more preferably, $C_2$alkyl. The compounds can be labelled with a detectable label, e.g., a radiolabel, e.g., tritium.

Another aspect of the invention relates to transgenic animals that express hPXR. For example, transgenic mice can be generated that express the hPXR gene as well as the endogenous mouse PXR gene. Mice can also be generated in which the endogenous PXR gene is knocked out and then replaced by the hPXR gene. Transgenic aminals can be generated that express isoforms of hPXR as well as mutant alleles of the gene. Transgenic animals developed by these methods can be used to screen compounds for drug interactions and toxicities, and to study the regulation of CYP3A in vivo.

A further aspect of the present invention relates to diagnostic assays that can be used to screen for mutations in hPXR that alter the ability of the receptor to induce CYP3A4 gene expression. These assays can be based on the sequencing of the hPXR gene, on hybridization approaches designed to detect sequence changes or polymorphisms, or the use of antibodies to distinguish wild-type from mutant/polymorphic hPXR. Changes that result in alteration of the DNA binding or ligand binding characteristics of hPXR can be expected to have a significant impact on hPXR activity. A mutation or polymorphism in hPXR can be indicative of a patient at increased risk of suffering an adverse reaction to a drug as a result of unusual rates of drug metabolism.

The invention also relates to antibodies, polyclonal or monoclonal, that are specific for hPXR, and antigen binding fragments thereof (e.g., Fab fragments). The antibodies can be generated in accordance with standard techniques using intact hPXR or a fragment thereof as defined above. The antibodies can be used, for example, in assays to detect the presence of the receptor. Further, the antibodies can be used in hPXR purification protocols.

The invention also relates to kits suitable for use, for example, in one or more method described above. The kits can include hPXR (or fragment thereof) or nucleic acid encoding same or antibodies as described above. The kit can also include compounds that bind hPXR, such as GW-485801. The hPXR, nucleic acid and/or antibody an be present in the kit disposed within a container means. The kit can also include ancillary reagents and buffers, etc., to facilitate practice of the specific method.

Certain aspects of the present invention are described in greater detail in the non-limiting Examples that follow.

EXAMPLES

The following experimental details are relevant to the specific Examples that follow.

Chemicals

Dexamethasone-t-butylacetate and RU486 were purchased from Research Plus, Inc. (Bayonne, N.J.) and Biomol (Plymouth Meeting, Pa.), respectively. All other compounds were purchased from either Sigma Chemical Co. (St. Louis, Mo.) or Steraloids, Inc. (Wilton, N.H.).

Molecular Cloning of hPXR cDNAs

An EST was identified in the Incyte database (clone identification number 2211526) that contained nucleotides 444-2111 of the hPXR sequence. An oligonucleotide derived from this EST sequence (5' CTGCTGCGCATCCAGGACAT 3') (SEQ ID NO:1) was used to screen a pCMV-SPORT human liver cDNA library (Gibco/BRL) using Gene Trapper solution hybridization cloning technology (Gibco/BRL). Two clones were obtained that encoded hPXR, one containing nucleotides 1-2125, the other containing nucleotides 102-2118. The sequence of the longer is shown in FIG. 1A-S*equences* were aligned and analyzed by the University of Wisconsin Genetics, Computer Group, programs.

Plasmids

The expression vector pSG5-hPXR was generated by PCR amplification and subcloning of nucleotides 1-1608 of the hPXR clone into the pSG5 expression vector (Strategene). pSG5-hPXR ATG was generated by PCR amplification of cDNA encoding amino acids 1-434 of hPXR using oligonucleotides 5'-GGGTGTGGGGAATCCACCACCATG-GAGGTGAGACCCAAAGAAAGC-3' (SEQ ID NO:2) (sense) and 5'-GGGTGTGGGGGATCCTCAGCTACCTGT-GATGCCG-3' (SEQ ID NO:3) (antisense) and insertion into EcoRI/BamHI-cut pSG5. The bacterial expression vector pGEX-hPXR was generated by PCR amplification of cDNA encoding amino acids 108-454 and insertion into pGEX-2T (Pharmacia). The reporter plasmid (DR3)$_4$-tk-CAT was generated by insertion of four copies of a double-stranded oligonucleotide containing the CYP3A1 DR3 PXRE (5'-GATCA-GACAGTTCATGAAGTTCATCTAGATC-3') (SEQ ID NO:4) into the BamHI site of PBLCAT2 (Luckow et al, Nucl. Acids Res. 15:5490 (1987)). The reporter plasmid (IR6)$_3$-tk-CAT was generated by insertion of three copies of the CYP3A4 IR6 PXRE (5'-GATCAATATGAACTCAAAG-GAGGTCAGTG-3') (SEQ ID NO:5) into the BamHI site of pBL2CAT. The pRSET-SRC1.14 expression plasmid has been previously described (Kliewer, S. A., et al. Cell 92:73-82 (1998)). All constructs were confirmed by sequence analysis.

Cotransfection Assays

CV-1 cells were plated in 24-well plates in DME medium supplemented with 10% charcoal-stripped fetal calf serum at a density of $1.2 \times 10^5$ cells per well. In general, transfection mixes contained 33 ng of receptor expression vector, 100 ng of reporter plasmid, 200 ng of β-galactosidase expression vector (pCH110, Pharmacia), and 166 ng of carrier plasmid. Cells were transfected overnight by lipofection using Lipofectamine (Life Technologies, Inc.), according to the manufacturer's instructions. The medium was changed to DME medium supplemented with 10% delipidated calf serum (Sigma) and cells were incubated for an additional 24 hours. Cell extracts were prepared and assayed for CAT and β-galactosidase activities as previously described (Lehmann et al, J. Biol. Chem. 270:12953-12.956 (1995)).

Northern Analysis

An approximately 1-0 kb fragment encoding the LBD of hPXR was [$^{32}$P]-labeled by random priming and used to probe mouse multiple tissue Northern blots (Clontech). Blots were hybridized in ExpressHyb solution (Clontech) at 42° C. overnight. Final washes were performed with 0.1×SSC, 0.1% SDS at 58° C.

Band Shift Assays hPXR, mPXR1, and hRXR were synthesized in vitro using the TNT rabbit reticulocyte lysate coupled in vitro transcription/translation system (Promega) according to the manufacturer's instructions. Gel mobility shift assays (20 µl) contained 10 mM Tris (pH 8.0), 40 mM KCl, 0.05% NP-40, 6% glycerol, 1 mM DTT, 0.2 µg of poly(dI-dC) and 2.5 µl each of in vitro synthesized. PXR and RXR proteins. Competitor oligonucleotides were included at a 10-fold or 50-fold excess. After a 10 min incubation on ice, 10 ng of [$^{32}$P]-labeled oligonucleotide was added and the incubation continued for an additional 10 min. DNA-protein complexes were resolved on a 4% polyacrylamide gel in 0.5×TBE (1×TBE=90 mM Tris, 90 mM boric acid, 2 mM EDTA). Gels were dried and subjected to autoradiography at −70° C. The following oligonucleotides were used as either radiolabeled probes or competitors (sense strand is shown):

```
                               (SEQ ID NO: 6)
CYP3A4 IR6:    5' GATCAATATGAACTCAAAGGAGGTCAGTG 3'

(SEQ ID NO: 7)
CYP3A4 IR6m1   5' GATCAATATGTTCTCAAAGGAGAACAGTG 3'

(SEQ ID NO: 8)
CYP3A4 IR6m2   5' GATCAATAACAACTCAAAGGAGGTCAGTG 3'

(SEQ ID NO: 9)
CYP3A1 DR3:    5' GATGCAGACAGTTCATGAAGTTCATCTAGAT
                  C 3'.
```

Carla

GST-hPXR fusion protein was expressed in BL21(DE3) plysS cells and bacterial extracts prepared by one cycle of freeze-thaw of the cells in Protein Lysis. Buffer containing 10 mM Tris, pH 8.0, 50 mM KCl, 10 mM DTT, and 1% NP-40 followed by centrifugation at 40,000×g for 30 minutes. Glycerol was added to the resulting supernatant to a final concentration of 10%. Lysates were stored at −80° C. [$^{35}$S]SRC1.14 was generated using the TNT rabbit reticulocyte system (Promega) in the presence of Pro-Mix (Amersham). Coprecipitation reactions included 25 µl of lysate containing GST-hPXR fusion protein, 25 µl Incubation Buffer (50 mM KCl, 40 mM HEPES pH 7.5, 5 mM β-mercaptoethanol, 1% Tween-20, 1% non-fat dry milk), 5 µl [$^{35}$S]SRC1.1A, and vehicle (1% DMSO) or compounds as indicated. The mixtures were incubated for 25 minutes at 4° C. with gentle mixing prior to the addition of 15 µl of glutathione-sepharose 4B beads (Pharmacia) that had been extensively washed with Protein Lysis Buffer. Reactions were incubated with gentle mixing at 4° C. for an additional 25 min. The beads were pelleted at 3000 rpm in a microfuge and washed 3 times with Protein Incubation Buffer containing either vehicle alone, dexamethasone-t-butylacetate, rifampicin, or clotrimazole. After the last wash, the beads were resuspended in 25 µl of 2×SDS-PAGE sample buffer containing 50 mM DTT. Samples were heated at 100° C. for 5 minutes and loaded onto a 10% Bis-Tris PAGE gel. Gels were dried and subjected to autoradiography.

Example 1

Molecular Cloning and Tissue Expression Pattern of hPXR

Figure 1C:
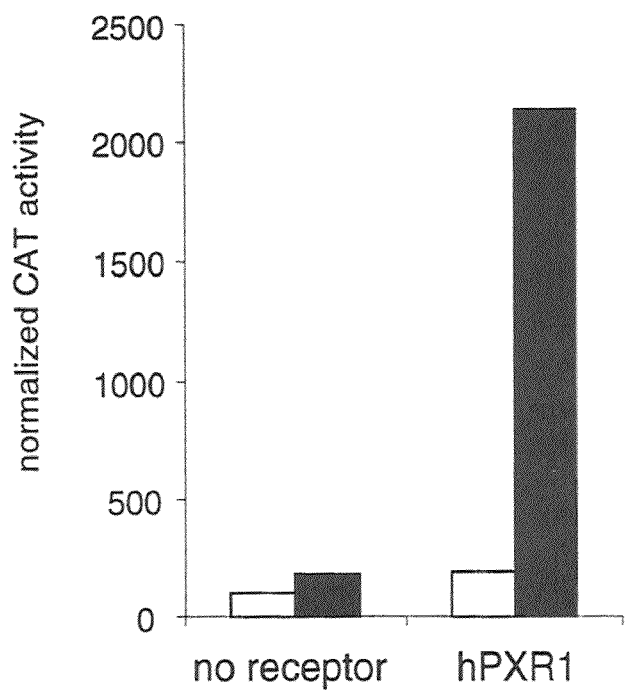

A human EST was identified in the Incyte LifeSeq® proprietary database that was highly homologous to a region of mPXR1 (Kliewer et al, Cell 92:73-82 (1998)). Two larger clones were isolated in a screen of a human liver cDNA library using an oligonucleotide within the EST as a probe. The longest of these clones was 2146 bp in length (FIG. 1A) and encoded a new member of the nuclear receptor superfamily that was 97% and 76% identical to mPXR1 in the DNA binding domain (DBD) and ligand binding domain (LBD), respectively (FIG. 1B). In terms of other members of the nuclear receptor superfamily, hPXR was most closely related to the *Xenopus laevis* orphan receptor ONR1 (Smith et al, Nucl. Acids Res. 22:66-71 (1994)) and the vitamin D receptor (FIG. 1B). Notably, the hPXR sequence lacked an AUG initiator codon in between an in-frame stop codon (nucleotides 205-207 in the hPXR sequence) and the start of the region encoding the DBD. However, transfection experiments performed in CV-1 cells with the hPXR clone and a reporter plasmid containing four copies of an established mPXR binding site from the rat CYP3A1 gene promoter inserted upstream of the minimal thymidine kinase (tk) promoter and the chloramphenicol acetyltransferase (CAT) gene (Kliewer et al, Cell 92:73-82 (1998)) demonstrated that the hPXR clone encoded a functional nuclear receptor that was activated efficiently by dexamethasone-t-butylacetate, a known mPXR1 ligand (Kliewer et al, Cell 92:73-82 (1998)) (FIG. 1C).

Figure 1D:
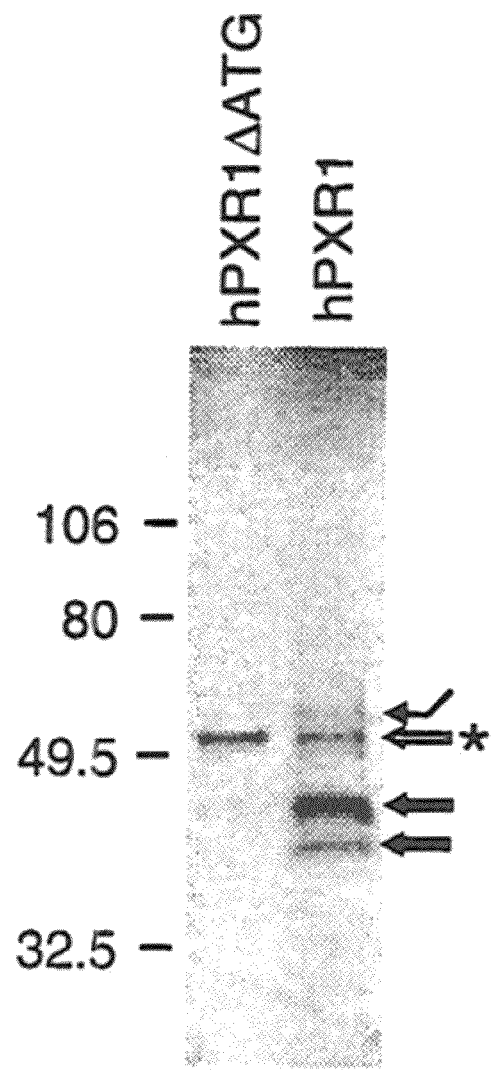

Examination of the hPXR sequence revealed an in-frame CUG codon (nucleotides 304-306) surrounded by a favorable Kozak sequence (Kozak, J. Biol. Chem. 266:19867-19870 (1991)). There is precedent for the use of CUG codons to initiate translation of eukaryotic proteins, including the nuclear receptor RARβ4 (Kozak, J. Biol. Chem. 266:19867-19870 (1991), Nagpal et al, Proc. Natl. Acad. Sci. USA 89:2718-2722 (1992)). Initiation of translation at this CUG codon would yield a protein of 434 amino acids, three longer than mRXR1, with a predicted MW of 49.7 kD. In order to determine whether translation of the hPXR cDNA initiated at the CUG codon, hPXR RNA containing the wild-type 5' region was translated in the presence of [$^{35}$S]methionine using rabbit reticulocyte lysates. As a control, hPXR RNA, in which this CUG codon had been mutated to the optimal AUG (hPXR AUG), was also translated in vitro. Translation of the wild-type hPXR RNA resulted in an approximately 50 kD protein that co-migrated with the translation product of hPXR AUG RNA (FIG. 1D, open arrow with asterisk). This 50 kD product was not produced when hPXR antisense RNA was used in the translation reaction. Much lower amounts of an approximately 53 kD translation product were also produced in translation reactions performed with hPXR RNA (FIG. 1D, bent arrow), indicating that a small amount of translation initiated at other non-AUG codons upstream of the CUG codon. However, the results indicate that the CUG codon represents the principal translation initiation site for hPXR containing a functional DBD.

Figure 2:
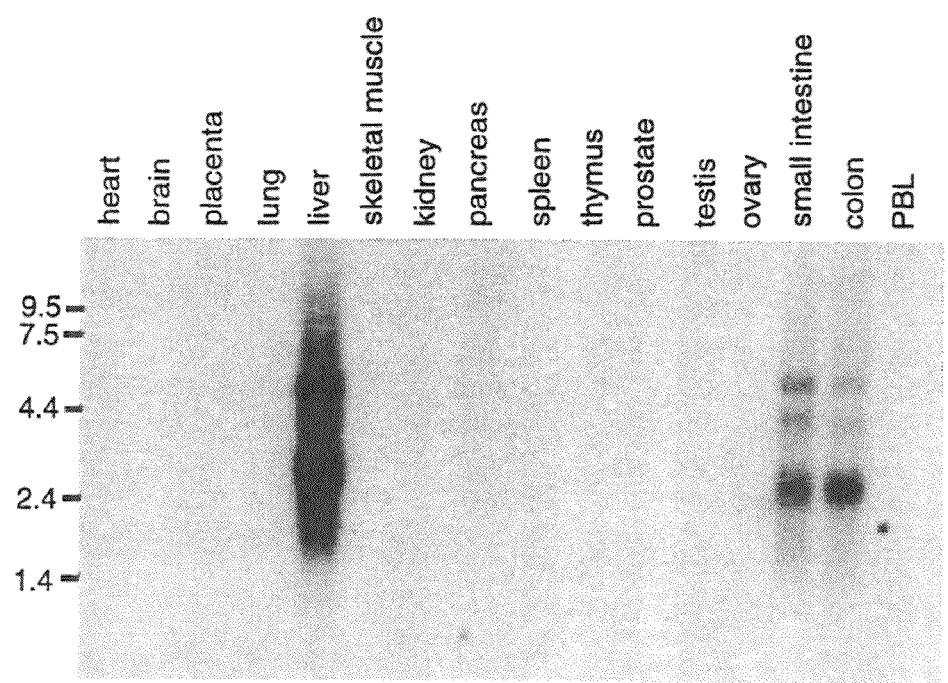
FIG. 2. Northern blot analysis of hPXR expression pattern in adult tissues (left to right, heart (1), brain (2), placenta (3), lung (4), liver (5), skeletal muscle (6), kidney (7), pancreas (8), spleen (9), thymus (10), prostate (11), testis (12), ovary (13), small intestine (14), colon (15), PBL (16). RNA size markers (in kb) are indicated at left.

The tissue expression pattern of hPXR was next examined via Northern analysis using blots containing poly(A)+ RNA prepared from multiple adult tissues. hPXR mRNA was expressed most abundantly in liver and was also present in the colon and small intestine (FIG. 2). Three transcripts of different size were detected in each of these tissues: a prominent 2.6 kb product and two less abundant messages of approximately 4.3 kb and 5 kb. It was recently shown that the mPXR gene is also abundantly expressed in liver and small intestine (Kliewer et al, Cell 92:73-82 (1998)). Whereas mPXR message was also detected at low levels in stomach and kidney, mRNA for hPXR was not detected in these tissues (FIG. 2). Thus, both hPXR and mPXR are most abundantly expressed in the liver and tissues of the gastrointestinal tract; however, there are differences in PXR expression patterns in mice and humans.

Example 2 hPXR Activates Transcription Through a Response Element in the CYP3A4 Gene Promoter Several lines of evidence have been provided that mPXR1 regulates CYP3A1 gene expression: mPXR1 was activated by compounds known to activate CYP3A1 gene expression including glucocorticoids and antiglucocorticoids, mPXR1 and CYP3A1 gene expression colocalized in the liver and small intestine, and mPXR1 bound to a response element in the CYP3A1 gene promoter that had previously been determined to confer responsiveness to glucocorticoids and antiglucocorticoids (Kliewer et al, Cell 92:73-82 (1998), Quattrochi et al, J. Biol. Chem. 270:28917-28923 (1995), Huss et al, J. Biol. Chem. 93:4666-4670 (1996)). The findings that the CYP3A4 gene is also expressed in the liver and intestine and that this expression is induced in response to glucocorticoids and antiglucocorticoids (Molawa et al, Proc. Natl. Acad. Sci, USA 83:5311-5315 (1986), Kocarek et al, Drug Met. Dispos. 23:415-421 (1995)) led to the investigation of whether hPXR regulates CYP3A4 gene expression.

Figure 3A:
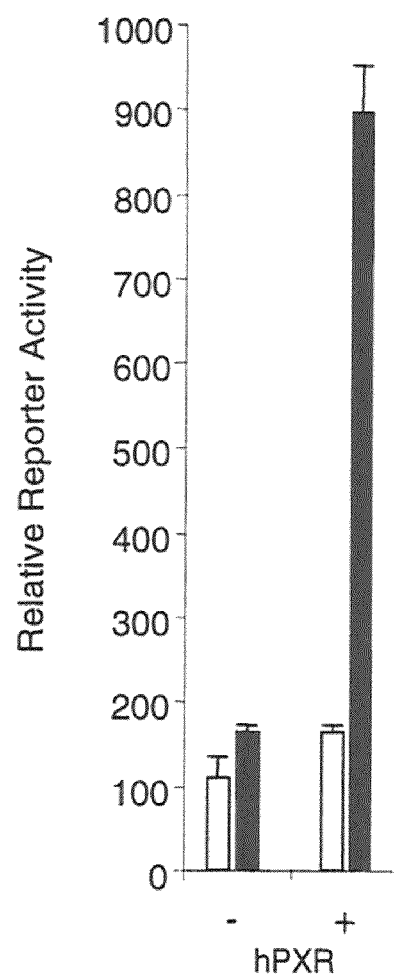
FIGS. 3A-3C. hPXR activates transcription through an IR6 element in the CYP3A4 promoter.
Figures 3B, 3C:
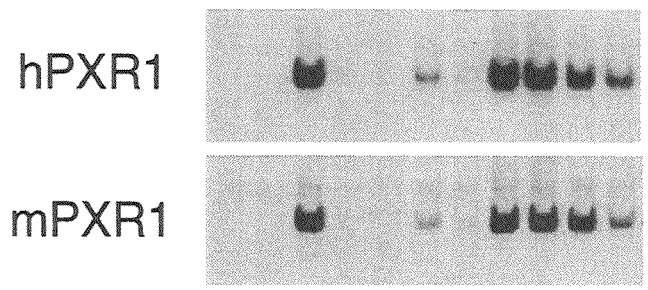

The induction of CYP3A4 expression in response to dexamethasone and rifampicin has been localized to an approximately 20 bp region of the promoter that contains two copies of the nuclear receptor half-site sequence AG(G/T)TCA organized as an inverted repeat (IR) and separated by 6 base pairs, an IR6 motif (Barwick et al, Molec. Pharmacol. 50:10-16 (1996)) (FIG. 3B). This IR6 motif is highly conserved in the promoters of CYP3A gene family members of several species (Barwick et al, Molec. Pharmacol. 50:10-16 (1996)). Interestingly, this half-site configuration is very different from that found in the CYP3A1 PXR response element (PXRE) which contains two half-sites organized as a direct repeat (DR) with a 3 nucleotide spacer, a DR3 motif (Kliewer et al, Cell 92:73-82 (1998)). To determine, whether hPXR could regulate transcription through the IR6 motif, a reporter plasmid was generated containing three copies of the CYP3A4 IR6 response element upstream of the tk promoter and CAT gene. Cotransfection assays were performed with the (IR6)$_3$-tk-CAT reporter and pSG5-hPXR ATG expression plasmids in CV-1 cells that were either treated with vehicle alone or 10 µM dexamethasone-t-butylacetate. hPXR induced reporter levels in the presence of dexamethasone-t-butylacetate (FIG. 3A), demonstrating that hPXR can activate transcription through the CYP3A4 IR6 motif.

In order to determine whether hPXR interacted directly with the CYP3A4 IR6 response element, band shift assays were performed. Since mPXR1 binds to DNA as a heterodimer with RXR (Kliewer et al, Cell 92:73-82 (1998)), it was suspected that hPXR would require RXR for high-affinity interactions with DNA. Neither hPXR nor RXR bound to a radiolabeled oligonucleotide containing the CYP3A4 IR6 motif on their own (FIG. 3C). However, hPXR and RXR bound efficiently as a heterodimer to the IR6 PXRE. The hPXR/RXR complex was competed efficiently by unlabeled oligonucleotides encoding either the IR6 PXRE from the CYP3A4 promoter or the DR3 PXRE from the CYP3A1 promoter that it was previously defined as a mPXR1/RXR binding site (Kliewer et al, Cell 92:73-82 (1998)) (FIG. 3C). Thus, the hPXR/RXR heterodimer interacted efficiently with two response elements with remarkably different architecture. Little or no competition was seen when competitor oligonucleotides were used that contained mutations in either the 5' half-site or both half-site sequences of the IR6 PXRE (FIG. 3C). The same binding profile was observed when the mPXR1 was substituted for hPXR (FIG. 3C). It was concluded from these experiments that hPXR binds efficiently to the CYP3A4 IR6 PXRE as, a heterodimer with RXR, and that hPXR and mPXR1 have very similar DNA binding profile.

Example 3

Differential Activation of Human and mPXR

Figure 4A:
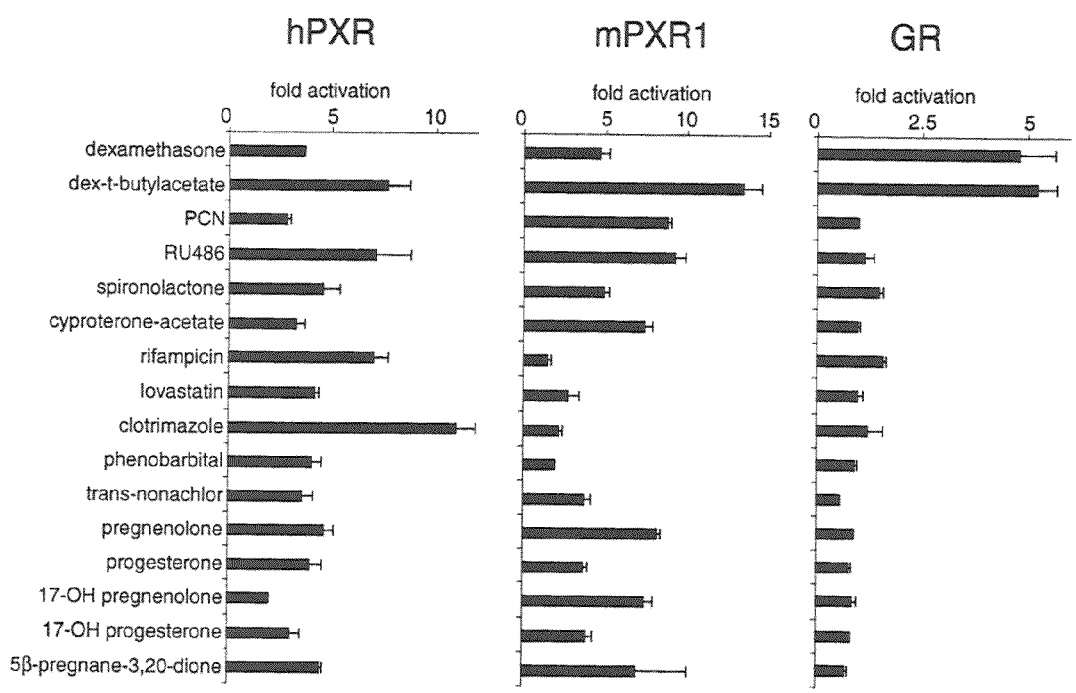
FIGS. 4A-4C. hPXR is activated by structurally-distinct inducers of CYP3A4 gene expression.
Figure 4B:
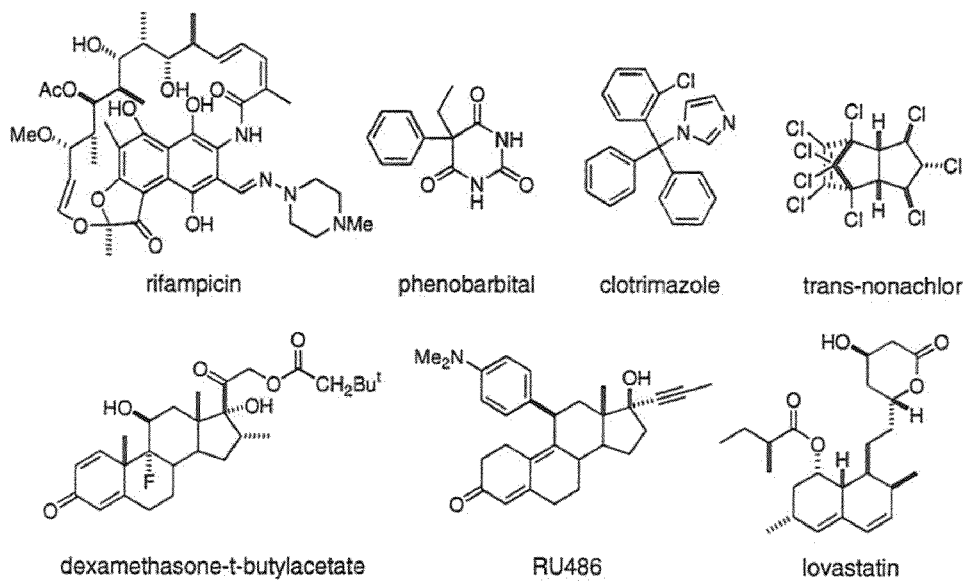

CYP3A4 gene expression is induced in response to a remarkable array of xenobiotics, including synthetic steroids (Kocarek et al., Drug Met. Dispos. 23:415-421 (1995), Schuetz et al, J. Biol. Chem. 259:2007-2012 (1984), Heuman et al, Mol. Pharmacol. 21:753-760 (1982), Schulte-Hermann et al, Cancer Res. 48:2462-2468 (1988)), macrolide antibiotics (Wrighton et al, Biochem. 24:2171-2178 (1985)), antimycotics (Hostetler et al, Mol. Pharmacol. 35:279-285 (1989)), HMG-CoA reductase inhibitors (statins) (Kocarek et al, Toxicol. Appl. Pharmacol. 120:298-307 (1993), Schuetz et al., Hepatology 18:1254-1262 (1993)), and phenobarbital-like compounds (Heuman et al, Mol. Pharmacol. 21:753-760 (1982)). It was next determined whether hPXR might mediate the effects of some or all of these compounds on CYP3A4 expression. CV-1 cells were cotransfected with the pSG5-hPXR ATG expression plasmid and the (IR6)$_3$-tk-CAT reporter plasmid, and the cells were treated with micromolar concentrations of a number of compounds that are known to induce CYP3A gene expression in humans and/or rodents. As shown in FIG. 4A, hPXR was activated by the synthetic steroids dexamethasone, dexamethasone-t-butylacetate, PCN, RU486, spironolactone, and cyproterone-acetate. Dexamethasone-t-butylacetate and RU486 were the most efficacious activators of hPXR among the synthetic steroids tested. Notably, the antibiotic rifampicin and the antimycotic clotrimazole were both efficacious activators of hPXR (FIG. 4A). The antihypercholesterolemic drug lovastatin also activated hPXR as did phenobarbital and the organochlorine pesticide transnonachlor (FIG. 4A). Thus, hPXR is activated by a remarkably diverse group of synthetic compounds that are known to induce CYP3A4 gene expression (FIG. 4B).

Several naturally-occurring C21 steroids were also tested on hPXR that were previously shown to activate mPXR1 (Kliewer et al, Cell 92:73-82 (1998)). Pregnenolone, progesterone, and 5 β-pregnane-3,20-dione all activated hPXR roughly 4-fold. The 17-hydroxy derivatives of pregnenolone and progesterone were weak activators of hPXR (FIG. 4A). These natural steroids all activated hPXR in transient transfection assays with EC$_{50}$ values >10 µM, suggesting that they are unlikely to be natural hPXR ligands. However, related pregnanes or pregnane metabolites may serve as natural hPXR ligands.

Analyses of the effects of chemical inducers of CYP3A gene expression in primary hepatocytes obtained from either rodents or humans have revealed significant interspecies differences (Barwick et al, Molec. Pharmacol. 50:10-16 (1996), Kocarek et al, Drug Met. Dispos. 23:415-421 (1995)). For example, rifampicin is an efficacious inducer of CYP3A4 gene expression in human hepatocytes but has little or no effect on CYP3A1 levels in rat hepatocytes. In contrast, PCN has marked effects on CYP3A levels in rat hepatocytes but only modest effects in human hepatocytes. To examine whether differences in PXR activation profiles might account for these interspecies variations, the same panel of compounds was tested on mPXR1. As shown in FIG. 4A, there were marked differences in the response profiles of the mouse and human homologs of PXR. Whereas rifampicin was an efficacious activator of hPXR, it was only a weak activator of mPXR1 (FIG. 4A). Clotrimazole, lovastatin and phenobarbital were also more efficacious activators of hPXR than mPXR1. In contrast, PCN only activated hPXR approximately 3-fold but activated mPXR1 roughly 9-fold (FIG. 4A). Taken together, these data indicate that much of the interspecies variability in CYP3A regulation may be due to differences in PXR activation profiles.

The panel of chemicals that induce CYP3A expression was also profiled on the human glucocorticoid receptor (GR). As shown in FIG. 4A, only dexamethasone and dexamethasone-t-butylacetate were efficacious activators of the GR. None of the other compounds activated the GR>1.5-fold (FIG. 4A). In contrast to a recent report (Calleja et al, Nature Med. 4:92-96 (1998)), activation of the GR by rifampicin was not observed. Since this previous work was performed in HepG2 cells, it may be that rifampicin is differentially metabolized in various cell lines. As expected, neither pregnenolone, progesterone, nor their 17-hydroxy derivatives had an effect on GR activity (FIG. 4A). Thus, the broad activation profile that was observed for the human and mouse homologs of PXR with inducers of CYP3A gene expression is not a general property of other steroid hormone receptors.

Figure 4C:
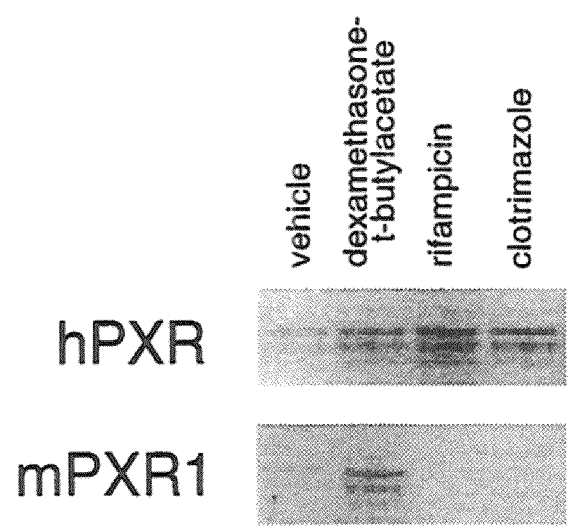
Figure 5:
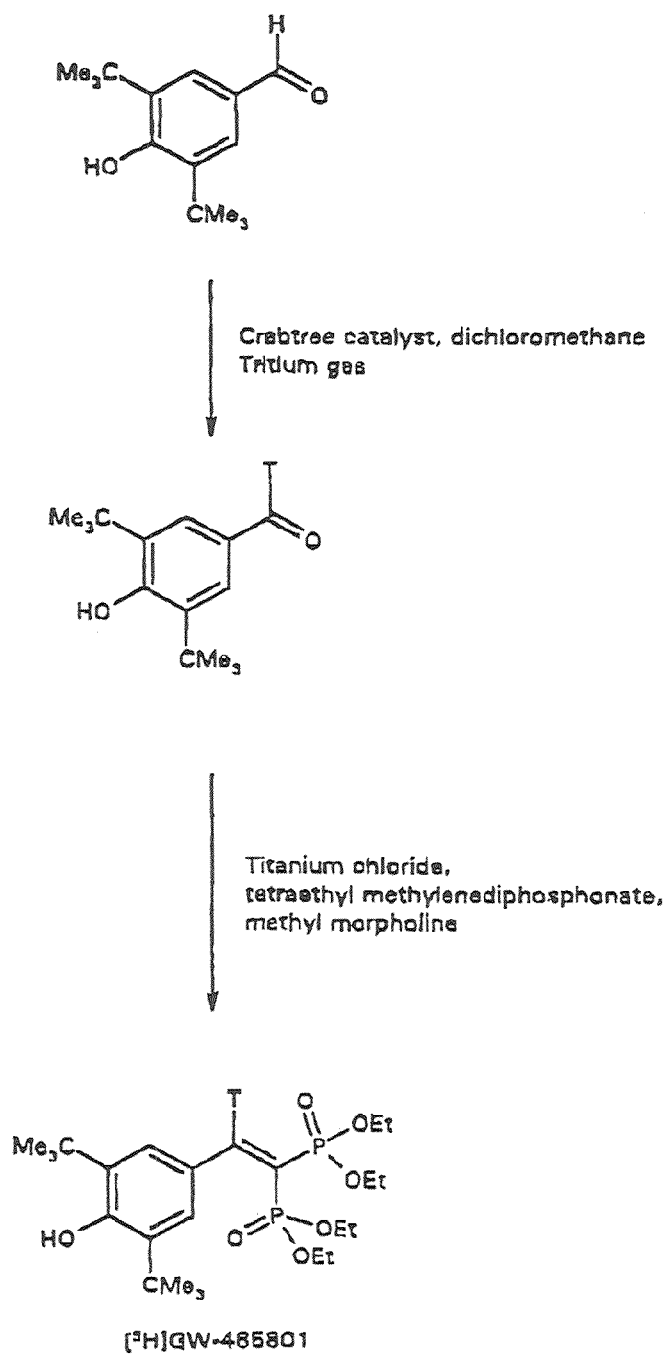
FIG. 5. Reaction scheme for production of [$^3$H]GW-485801.

In the absence of high-affinity radioligands, coactivator-based assays have been used as a biochemical means to determine whether compounds that activate orphan nuclear receptors do so through direct interactions with the protein (Kliewer et al, Cell 92:73-82 (1998), Krey et al, Mol. Endocrinol. 11:779-791 (1997)). These assays are predicated on the finding that ligands induce the interaction of nuclear receptors with accessory proteins, termed coactivators (Krey et al, Mol. Endocrinol. 11:779-791 (1997)). It was recently demonstrated that several steroidal activators of mPXR1, including dexamethasone-t-butylacetate and PCN, promote the interaction of the mPXR1 LBD with a 14 kD fragment of the steroid receptor coactivator 1 (SRC1.14) (Kliewer et al, Cell 92:73-82 (1998)). In order to examine whether the structurally-diverse compounds that activate hPXR do so by acting as ligands, three of the more potent activators representing different chemical classes were selected, dexamethasone-t-butylacetate, rifampicin, and clotrimazole, for testing in the coactivator-receptor ligand assay (CARLA. The LBDs of hPXR and mPXR1 were expressed in *E. coli* as fusion proteins with glutathione-S-transferase (GST), and SRC1.14 was synthesized in vitro in the presence of [$^{35}$S]methionine and [$^{35}$S]cysteine. As shown, in FIG. 4C, dexamethasone-t-butylacetate, rifampicin and clotrimazole each promoted the interaction of [$^{35}$S]SRC1.14 with GST-hPXR. Consistent with the results of the transfection studies, dexamethasone-t-butylacetate induced an efficient interaction between GST-mPXR1 and [$^{35}$S]SRC1.14 whereas rifampicin and clotrimazole did not (FIG. 4C). Taken together, these data indicate that structurally-divergent compounds can serve as hPXR ligands, and that the human and mouse homologs of PXR differ significantly in terms of their ligand binding properties.

Example 4

Transfection Assay

Plasmids: GAL4-hPXR chimera and UAS-tk-SPAP reporters. The GAL4-hPXR expression constructs contain the translation initiation sequence and amino acids 1 to 147 of the yeast *S. crevisiae* transcription factor GAL4 in the pSG5 expression vector (Statagene). Amino acids 108 to 434 of hPXR are amplified by polymerase chain reaction (PCR) using vent polymerase (New England Biolads) and inserted C-terminal to the GAL4 sequences. The UAS-tk-SPAP reporter contains 5 copies of the GAL4 binding site upstream of the tk promoter and the CAT gene (Berger et al, Gene 66:1 (1988)).

Transfection assay: SPAP reporter. CV-1 cells are plated in DME medium supplemented with 10% delipidated fetal calf serum at a density of $2.4 \times 10^4$ cells per well in a 96-well plate (Costar) 16-24 h before transfection. In general, 8.0 ng of reporter plasmid, 25.0 ng of β-galactosidase expression vector (pCH110, Pharmacia), and 2.0 ng of GAL4-hPXR expression vector are mixed with carrier DNA (pBluescript, Stratagene) to a total of 80 ng of DNA per well in a volume of 10 ml optiMEM I medium (Life Technologies). To this, a second mix, containing 9.3 ml optiMEM I medium and 0.7 ml of LIPOFECTAMINE™ (Life Technologies), is added. After 30 min., an additional 80 ml of optiMEM I medium are added and the combined mix is then applied to the cells. Sixteen hours later, the medium is changed to DME medium supplemented with 10% delipidated and heat inactivated fetal calf serum and the test compound at a concentration of $10^{-5}$M. After incubation for 24 h, SPAP activity and β-galactosidase activity are measured by directly adding to the medium 200 ml substrate mix (16 mM o-nitrophenyl β-D-galactopyranoside (Sigma), 120 mM fluorescein diphosphate (Molecular Probes), 0.16% Triton X-100, 160 mM diethanolamine pH9, 44.8 mM NaCl, and 0.8 mM $MgCl_2$). Alternatively, alkaline phosphatase and β-galactosidase activities are measured separately using standard protocols. Briefly, cells are lysed by adding 25 ml 0.5% Triton X-100 to the supernatant. To 40 ml cell lysate, 200 ml β-galactosidase substrate reagent (36 mM o-nitrophenyl β-D-galactopyranoside, 1.25 mM $MgCl_2$, 2.8 mM NaCl, 4.4M β-mercaptoethanol) or 200 ml alkaline phosphatase substrate reagent (2.5 mM p-nitrophenyl phosphate, 0.5 mM $MgCl_2$, 20 mM NaCl, 1 M diethanolamine pH 9.85) are added and incubated for 1 h. Alkaline phosphatase activity is expressed as fold activation relative to that observed with vehicle alone (normalized to β-galactosidase activity which serves as internal control standard for transfection efficiency).

Example 5

Synthesis of [$^3$H]GW-485801

(i) The Preparation of [$^3$H]3,5-Ditertbutyl-4-hydroxy benzaldehyde.

3,5-Diterbutyl-4-hydroxy benzaldehyde, 5 mg (20.6 μmol) and Crabtree catalyst, 7.5 mg (9.3 μmol), were dissolved in 2 ml dichloromethane and stirred under 10 Ci tritium gas for 5 hours. The solution was then evaporated to dryness, and labile tritium was removed by repeated evaporations from methanol. The residue was redissolved in methanol, 10 ml, counted and analyzed.

Yield=800 mCi.

Radiochemical purity by TLC on silica in hexane:ethyl acetate (80:20) was approximately 50%.

The crude material was evaporated to 1 ml and purified by preparative plate chromatography on a single 500 μm silica plate, eluting in hexane:ethyl acetate (85:15). The plates were viewed under the band corresponding to required aldehyde was collected and the product extracted into ethyl acetate.

This was evaporated to dryness and redissolved in dichloromethane, counted and analyzed.

Yield=370 mCi.

TLC as above showed a singly labelled, specific activity 23 Ci/mmol.

(ii) The Preparation of [³H]GW-485801

The product from (i) above (370 mCi at 23 Ci/mmol, 16 µmol) was evaporated to dryness, redissolved in THF, 1 ml, and cooled in an ice bath with stirring. 1M Titanium (IV) chloride in toluene, 55 µl, 55 µmol, was added, immediate yellow color formed. Tetraethyl methylenediphosphonate, 75 µl, of a THF solution at 110 mg/ml, 28.6 µmol, was added, followed by N-methyl morpholine, 8.1 µl, 7.5 mg, 74 µmol. This caused a deep blue color. The solution was then stirred at room temperature for 4 hours.

TLC analysis on silica in ethyl acetate:methanol (90:10) showed approximately 60% the radioactivity to correspond to inactive GW-485801.

(iii) The Purification of [³H]GW-485801

The crude product was purified by preparative plate chromatography on 2×1 mm silica plates, eluting in ethyl acetate:methanol (90:10). The plates were viewed under UV, the band corresponding to required product was collected and the product extracted into ethyl acetate:methanol (90:10). This was evaporated to dryness and redissolved in nitrogen-flushed ethanol, 30 ml. This was a yellow solution.

Yield=180 mCi.

(iv) The Analysis of [³H]GW-485801

The purified product resulting from (iii) was analyzed by TLC, HPLC, mass spectroscopy and T-NMR.

TLC showed a radiochemical purity of 99%.

HPLC showed a radiochemical purity of 98.9%.

In both of the above systems, the radioactive peak co-eluted with inactive GW-485801.

Mass spectroscopy showed a specific activity of 23 Ci/mmol, the isotope distribution being 18.4% unlabelled, 81.6% 1×³H. The spectrum of the radioactive material was consistent with that of the inactive GW-485801.

T-NMR showed a single labelling position (peak split into four signals by coupling to the phosphorus atoms) corresponding to labelling in the vinylic position of GW-485801. This corresponds to labelling in the aldehyde-H in the precursor.

A portion of the material was diluted to 1 mCi/ml with nitrogen-flushed ethanol and dispensed as 1×2 mCi pack. The remainder was stored at –20° C. (approximately 170 mCi).

Example 6

Biotin-His6-PXR/RXRa Protein

The coding sequence representing amino acids 130-434 of human PXR (Genbank AF061056) was subcloned into the pRSETa expression vector (Invitrogen). Sequence encoding a polyhistidine tag derived from an N-terminal PCR primer (MKKGHHHHHHG) (SEQ ID NO:10) was fused in-frame. The resulting encoded His6-PXR sequence was as follows:

```
                                         (SEQ ID NO: 11)
MKKGHHHHHHGSERTGTQPLGVQGLTEEQRMMIRELMDAQMKTF

DTTFSHFKNFRLPGVLSSGCELPESLQAPSREEAAKWSQVRKDL

CSLKVSLQLRGEDGSVWNYKPPADSGGKEIFSLLPHMADMSTYM

FKGIISFAKVISYFRDLPIEDQISLLKGAAFELCQLRFNTVFNA
```

-continued
```
ETGTWECGRLSYCLEDTAGGFQQLLLEPMLKFHYMLKKLQLHEE

EYVLMQAISLFSPDRPGVLQHRVVDQLQEQGAITLKSYIECNRP

QPAHRFLFLKIMAMLTELRSINAQHTQRLLRIQDIHPFATPLMQ

ELFGITGS.
```

Restriction enzymes Nde I and Hind III were used to release the cDNA fragment encoding amino acids 225-462 of RXRα from BB5508 (pRSETa). The fragment was ligated into the like-cut pET24a expression plasmid (Novagen). The Bgl II, Hind III fragment (contains T7 promoter, lac operator, RBS and RXRa) of this construct was then cloned into the BamH I, Hind III sites (removes tetracycline resistance) of pACYC184 (BB5114). This allows for expression of RXRα from the T7 promoter when grown in BL21(DE3) cells and induced with IPTG. The resulting encoded RXRα sequence was as follows:

```
                                         (SEQ ID NO: 12)
MKKGSANEDMPVERILEAELAVEPKTETYVEANMGLNPSSPNDP

VTNICQAADKQLFTLVEWAKRIPHFSELPLDDQVILLRAGWNEL

LIASFSHRSIAVKDGILLATGLHVHRNSAHSAGVGAIFDRVLTE

LVSKMRDMQMDKTELGCLRAIVLFNPDSKGLSNPAEVEALREKV

YASLEAYCKHKYPEQPGRFAKLLLRLPALRSIGLKCLEHLFFFK

LIGDTPIDTFLMEMLEAPHQMT.
```

The His6-PXR/pRSETa and RXRα/pACYC184 plasmids were cotransformed into the BL21(DE3) E. coli strain. One-liter shake flask liquid cultures containing standard Luria-Bertani (LB) broth with 0.5 mg/ml Ampicillin and 0.05 mg/ml Chloramphenicol were inoculated and grown at 22° C. for 24 hours. The cells were induced with 0.05 mM IPTG for 4-6 hours at 22° C. then the cells were harvested by centrifugation (20 minutes, 3500 g, 4° C.). The cell pellet was stored at –80° C. The cell pellet was resuspended in 250 ml Buffer A (50 mM Tris-Cl pH8.0, 250 mM NaCl, 50 mM imidazole pH7.5). Cells were sonicated for 3-5 minutes on ice and the cell debris was removed by centrifugation (45 minutes, 20,000 g, 4° C.). The cleared supernatant was filtered through a 0.45 mM filter and loaded on to a 50 ml ProBond [Ni⁺⁺ charged] chelation resin (Invitrogen). After washing to baseline with Buffer A, the column was washed with Buffer A containing 125 mM imidazle pH 7.5. The His6-PXR/RXRα complex was eluted from the column using Buffer A with 300 mM imidazole pH 7.5. Column fractions were pooled and concentrated using Centri-prep 30K (Amicon) units. The protein was subjected to size exclusion, using a column (26 mm ×90 cm) packed with Sepharose S-75 resin (Pharmacia) pre-equilibrated with 20 mM Tris-Cl pH 8.0, 200 mM NaCl, 5 mM DTT, 2.5 mM EDTA, pH 8.0. Column fractions were pooled and concentrated as before. The purified His6-PXR/RXRα was buffer exchanged by gel filtration into PBS, resulting in an average total molar protein concentration of 45 mM. A five-fold total molar excess of NHS-LC-Biotin (Pierce) was added to this protein mixture in a minimal volume of PBS. This solution was incubated with gentle mixing for 60 minutes at ambient temperature, approximately 23° C. The biotinylation modification reaction was stopped by the addition of a 2000× molar excess of Tris-HCl, pH 8. The biotin-His6-PXR/RXRα was dialyzed at 4° C. against 3 buffer changes, each of at least 50 volumes, TBS pH 8 containing 5 mM DTT, 2 mM EDTA and 2% sucrose. The biotin-His6-PXR/RXRα was subjected to mass spectrometric analysis to reveal the extent of modification by the reagent. The biotinylated protein solution was frozen and stored at −80° C.

Example 7

PXR Scintillation Proximity Assay (SPA)

Streptavidin-PVT SPA beads (AmershamPharmacia cat # RPNQ0007) were resuspended in assay buffer (50 mM Tris HCl pH 8.0, 50 mM KCl, 1 mM DTT, 0.1 mg/ml essentially fatty acid free bovine serum albumin) at 0.5 mg/ml. Biotin-His6-PXR/RXRα was added to the beads to a final concentration of 50 nM. The receptors were allowed to couple to the SPA beads for thirty minutes at room temperature. The uncoupled receptor was removed by centrifuging the SPA beads at 3000 rpm for 5 minutes in a swinging bucket rotor of a Rupp & Bowman Silencer centrifuge. The receptor coated SPA beads were then resuspended in assay buffer to 3.3 mg/ml. 100 μg (30 μL) of receptor coated SPA beads was added to each well of a 96-well Optiplate (Packard cat # 6005190). Each well also contained [$^3$H]GW-485801, at final concentrations ranging from 0.5 nM to 800 nM. Non-specific binding was determined by addition of 10 μM clotrimazole. The total volume in each well was 100 μL. The plates were sealed with TopSealA (Packard cat #6005185) and agitated momentarily to ensure complete mixing. The plates were then allowed to incubate at room temperature until equilibrium was obtained. The plates were then counted on a TopCount liquid scintillation counter (Packard) using a protocol optimized for $^3$H PVT SPA. Triplicate samples in the absence (T samples) or presence (NS samples) of clotrimazole were averaged and specific binding was calculated using the equation:

specific binding=T−NS

Figure 6:
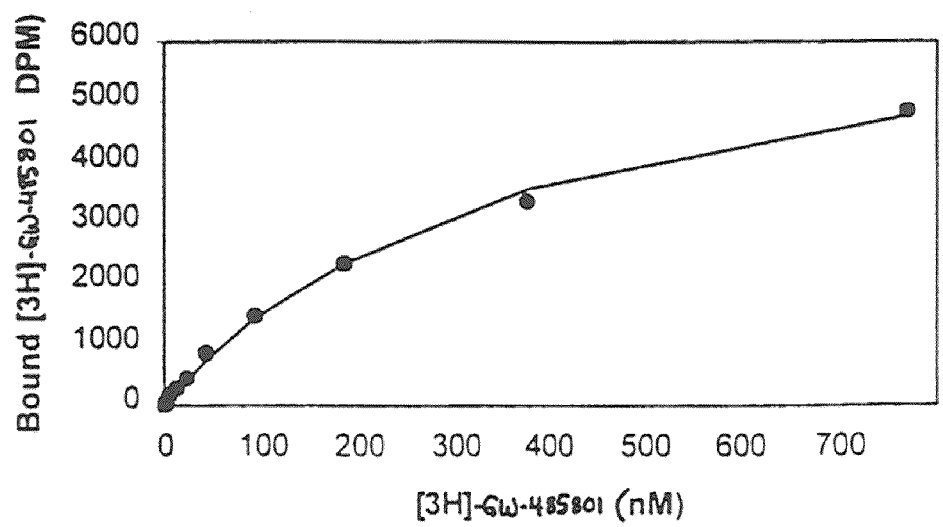
FIG. 6. Plot of specific binding vs. concentration of [$^3$H] GW-485801. Kd=370 nM.

Plots of specific binding vs concentration of [$^3$H]GW-485801 were generated (FIG. 6). Kd values were determined using non-linear regression when the data were fit to the equation of a rectangular hyperbola.

Test compounds were dissolved in DMSO at 10 mM and diluted 1:10 in DMSO before serially diluting in assay buffer. Compounds were typically tested at concentrations ranging from 100 μM to 0.3 nM. Streptavidin-PVT SPA beads (AmershamPharmacia cat 4 RPNQ0007) were resuspended in assay buffer (50 mM Tris HCl pH 8.0, 50 mM KCl, 1 mM DTT, 0.1 mg/ml essentially fatty acid free bovine serum albumin) at 0.5 mg/ml. Biotin-His6-PXR/RXRα was added to the beads to a final concentration of 50 nM. The receptors were allowed to couple to the SPA beads for thirty minutes at room temperature. The uncoupled receptor was removed by centrifuging the SPA beads at 3000 rpm for 5 minutes in a swinging bucket rotor of a Rupp & Bowman Silencer centrifuge. The receptor coated SPA beads were then resuspended in assay buffer to 3.3 mg/ml. 100 μg (30 μL) of receptor coated SPA beads was added to each well of a 96-well Optiplate (Packard cat # 6005190). Each well also contained [$^3$H]GW-485801 at a final concentration of 25 nM and test compound or an equal volume of assay buffer. Non-specific binding was determined by addition of 10 μM clotrimazole. The total volume in each well was 100 μL. The plates were sealed with TopSealA (Packard cat #6005185) and agitated momentarily to ensure complete mixing. The plates were then allowed to incubate at room temperature until equilibrium was obtained, approximately 1.5 hours. The plates were then counted on a Top-Count liquid scintillation counter (Packard) using a protocol optimized for $^3$H PVT SPA and programmed to correct for color quenching. Values for "% [$^3$H]GW-485801 Bound" were calculated using the following equation:

$$[^3\text{H}]GW\text{-}485801 \text{ Bound}=100*[(C_{DPM}-NS_{DPM})/(T_{DPM}-NS_{DPM})]$$

where $C_{DPM}$ is the DPM value from a well containing a test compound, $NS_{DPM}$ is the average of the DPM values from the "non-specific" wells which contained 10 μM clotrimazole, $T_{DPM}$ is the average of the DPM values from the "total" wells which contained no added compounds. Graphs of %[$^3$H]GW-485801 Bound vs concentration were' generated for each test compound and IC50 values were determined using non-linear regression (see Table 1).

TABLE 1

| Compound | IC50 (μM) |
| --- | --- |
| GW-485801 | 0.58 |
| Clotrimazole | 1.3 |
| Rifampicin | 2.4 |
| 5b-pregnane-3,20-dione | 1.0 |

All documents cited above are hereby incorporated in their entirety by reference.

One skilled in the art will appreciate from a reading of this disclosure that various changes in form and detail can be made without departing from the true scope of the invention.

What is claimed is:

1. A method of screening a test compound for its ability to activate or inhibit hPXR comprising:
   i) preparing an expression vector comprising a sequence encoding a DNA binding domain and a hPXR ligand binding domain having the amino acid sequence of 141-434 of SEQ ID NO: 14;
   ii) preparing a reporter construct comprising a DNA binding site recognized by said DNA binding domain operably linked to a reporter gene,
   iii) introducing said expression vector and said reporter construct into compatible host cells,
   iv) incubating said cells resulting from step (iii) with said test compound, and
   v) determining the level of expression of said reporter gene, wherein enhancement of expression of said reporter gene in the presence of said test compound indicates that said test compound can activate hPXR, and wherein inhibition of expression of said reporter gene in the presence of said test compound indicates that said test compound can inhibit hPXR.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: probe

<400> SEQUENCE: 1
ctgctgcgca tccaggacat                                         20

<210> SEQ ID NO 2
<211> LENGTH: 45

```
<212> TYPE: DNA
<213> ORGANISM: Artificial Sequence
<220> FEATURE:
<223> OTHER INFORMATION: Probe

<400> SEQUENCE: 2
gggtgtgggg aatccaccac catggaggtg agacccaaag aaagc            45

<210> SEQ ID NO 3
<211> LENGTH: 34
<212> TYPE: DNA
<213> ORGANISM: Artificial Sequence
<220> FEATURE:
<223> OTHER INFORMATION: Probe

<400> SEQUENCE: 3
gggtgtgggg gatcctcagc tacctgtgat gccg                        34

<210> SEQ ID NO 4
<211> LENGTH: 31
<212> TYPE: DNA
<213> ORGANISM: Artificial Sequence
<220> FEATURE:
<223> OTHER INFORMATION: Probe

<400> SEQUENCE: 4
gatcagacag ttcatgaagt tcatctagat c                           31

<210> SEQ ID NO 5
<211> LENGTH: 29
<212> TYPE: DNA
<213> ORGANISM: Artificial Sequence
<220> FEATURE:
<223> OTHER INFORMATION: Probe

<400> SEQUENCE: 5
gatcaatatg aactcaaagg aggtcagtg                              29

<210> SEQ ID NO 6
<211> LENGTH: 29
<212> TYPE: DNA
<213> ORGANISM: Artificial Sequence
<220> FEATURE:
<223> OTHER INFORMATION: Probe

<400> SEQUENCE: 6
gatcaatatg aactcaaagg aggtcagtg                              29

<210> SEQ ID NO 7
<211> LENGTH: 29
<212> TYPE: DNA
<213> ORGANISM: Artificial Sequence
<220> FEATURE:
<223> OTHER INFORMATION: Probe

<400> SEQUENCE: 7
gatcaatatg ttctcaaagg agaacagtg                              29

<210> SEQ ID NO 8
<211> LENGTH: 29
<212> TYPE: DNA
<213> ORGANISM: Artificial Sequence
<220> FEATURE:
<223> OTHER INFORMATION: Probe

<400> SEQUENCE: 8
gatcaataac aactcaaagg aggtcagtg                              29
```

<210> SEQ ID NO 9
<211> LENGTH: 32
<212> TYPE: DNA
<213> ORGANISM: Artificial Sequence
<220> FEATURE:
<223> OTHER INFORMATION: Probe

<400> SEQUENCE: 9
gatgcagaca gttcatgaag ttcatctaga tc                     32

<210> SEQ ID NO 10
<211> LENGTH: 11
<212> TYPE: PRT
<213> ORGANISM: Artificial Sequence
<220> FEATURE:
<223> OTHER INFORMATION: poly histadine tag

<400> SEQUENCE: 10

Met Lys Lys Gly His His His His His His Gly
 1               5                  10

<210> SEQ ID NO 11
<211> LENGTH: 316
<212> TYPE: PRT
<213> ORGANISM: Artificial Sequence
<220> FEATURE:
<223> OTHER INFORMATION: His6-PXR Fusion Protein

<400> SEQUENCE: 11

Met Lys Lys Gly His His His His His Gly Ser Glu Arg Thr Gly
 1               5                  10                  15

Thr Gln Pro Leu Gly Val Gln Gly Leu Thr Glu Glu Gln Arg Met Met
            20                  25                  30

Ile Arg Glu Leu Met Asp Ala Gln Met Lys Thr Phe Asp Thr Thr Phe
        35                  40                  45

Ser His Phe Lys Asn Phe Arg Leu Pro Gly Val Leu Ser Ser Gly Cys
    50                  55                  60

Glu Leu Pro Glu Ser Leu Gln Ala Pro Ser Arg Glu Glu Ala Ala Lys
65                  70                  75                  80

Trp Ser Gln Val Arg Lys Asp Leu Cys Ser Leu Lys Val Ser Leu Gln
                85                  90                  95

Leu Arg Gly Glu Asp Gly Ser Val Trp Asn Tyr Lys Pro Pro Ala Asp
            100                 105                 110

Ser Gly Gly Lys Glu Ile Phe Ser Leu Leu Pro His Met Ala Asp Met
        115                 120                 125

Ser Thr Tyr Met Phe Lys Gly Ile Ile Ser Phe Ala Lys Val Ile Ser
    130                 135                 140

Tyr Phe Arg Asp Leu Pro Ile Glu Asp Gln Ile Ser Leu Leu Lys Gly
145                 150                 155                 160

Ala Ala Phe Glu Leu Cys Gln Leu Arg Phe Asn Thr Val Phe Asn Ala
                165                 170                 175

Glu Thr Gly Thr Trp Glu Cys Gly Arg Leu Ser Tyr Cys Leu Glu Asp
            180                 185                 190

Thr Ala Gly Gly Phe Gln Gln Leu Leu Leu Glu Pro Met Leu Lys Phe
        195                 200                 205

His Tyr Met Leu Lys Lys Leu Gln Leu His Glu Glu Glu Tyr Val Leu
    210                 215                 220

Met Gln Ala Ile Ser Leu Phe Ser Pro Asp Arg Pro Gly Val Leu Gln
225                 230                 235                 240

```
His Arg Val Val Asp Gln Leu Gln Glu Gln Phe Ala Ile Thr Leu Lys
                245                 250                 255

Ser Tyr Ile Glu Cys Asn Arg Pro Gln Pro Ala His Arg Phe Leu Phe
            260                 265                 270

Leu Lys Ile Met Ala Met Leu Thr Glu Leu Arg Ser Ile Asn Ala Gln
        275                 280                 285

His Thr Gln Arg Leu Leu Arg Ile Gln Asp Ile His Pro Phe Ala Thr
    290                 295                 300

Pro Leu Met Gln Glu Leu Phe Gly Ile Thr Gly Ser
305                 310                 315

<210> SEQ ID NO 12
<211> LENGTH: 242
<212> TYPE: PRT
<213> ORGANISM: Artificial Sequence
<220> FEATURE:
<223> OTHER INFORMATION: RXR Alpha Protein

<400> SEQUENCE: 12

Met Lys Lys Gly Ser Ala Asn Glu Asp Met Pro Val Glu Arg Ile Leu
 1               5                  10                  15

Glu Ala Glu Leu Ala Val Glu Pro Lys Thr Glu Thr Tyr Val Glu Ala
             20                  25                  30

Asn Met Gly Leu Asn Pro Ser Ser Pro Asn Asp Pro Val Thr Asn Ile
         35                  40                  45

Cys Gln Ala Ala Asp Lys Gln Leu Phe Thr Leu Val Glu Trp Ala Lys
     50                  55                  60

Arg Ile Pro His Phe Ser Glu Leu Pro Leu Asp Asp Gln Val Ile Leu
 65                  70                  75                  80

Leu Arg Ala Gly Trp Asn Glu Leu Leu Ile Ala Ser Phe Ser His Arg
                 85                  90                  95

Ser Ile Ala Val Lys Asp Gly Ile Leu Leu Ala Thr Gly Leu His Val
            100                 105                 110

His Arg Asn Ser Ala His Ser Ala Gly Val Gly Ala Ile Phe Asp Arg
        115                 120                 125

Val Leu Thr Glu Leu Val Ser Lys Met Arg Asp Met Gln Met Asp Lys
    130                 135                 140

Thr Glu Leu Gly Cys Leu Arg Ala Ile Val Leu Phe Asn Pro Asp Ser
145                 150                 155                 160

Lys Gly Leu Ser Asn Pro Ala Glu Val Glu Ala Leu Arg Glu Lys Val
                165                 170                 175

Tyr Ala Ser Leu Glu Ala Tyr Cys Lys His Lys Tyr Pro Glu Gln Pro
            180                 185                 190

Gly Arg Phe Ala Lys Leu Leu Leu Arg Leu Pro Ala Leu Arg Ser Ile
        195                 200                 205

Gly Leu Lys Cys Leu Glu His Leu Phe Phe Phe Lys Leu Ile Gly Asp
    210                 215                 220

Thr Pro Ile Asp Thr Phe Leu Met Glu Met Leu Glu Ala Pro His Gln
225                 230                 235                 240

Met Thr

<210> SEQ ID NO 13
<211> LENGTH: 2146
<212> TYPE: DNA
<213> ORGANISM: Artificial Sequence
<220> FEATURE:
<223> OTHER INFORMATION: Probe
```

<400> SEQUENCE: 13

```
tgaaatatag gtgagagaca agattgtctc atatccgggg aaatcataac ctatgactag      60
gacgggaaga ggaagcactg cctttacttc agtgggaatc tcggcctcag cctgcaagcc     120
aagtgttcac agtgagaaaa gcaagagaat aagctaatac tcctgtcctg aacaaggcag     180
cggctccttg gtaaagctac tccttgatcg atcctttgca ccggattgtt caaagtggac     240
cccaggggag aagtcggagc aaagaactta ccaccaagca gtccaagagg cccagaagca     300
aacctggagg tgagacccaa agaaagctgg aaccatgctg actttgtaca ctgtgaggac     360
acagagtctg ttcctggaaa gcccagtgtc aacgcagatg aggaagtcgg aggtccccaa     420
atctgccgtg tatgtgggga caaggccact ggctatcact tcaatgtcat gacatgtgaa     480
ggatgcaagg gcttttcag gagggccatg aaacgcaacg cccggctgag gtgccccttc     540
cggaagggcg cctgcgagat cacccggaag acccggcgac agtgccaggc ctgccgcctg     600
cgcaagtgcc tggagagcgg catgaagaag gagatgatca tgtccgacga ggccgtggag     660
gagaggcggg ccttgatcaa gcggaagaaa agtgaacgga cagggactca gccactggga     720
gtgcaggggc tgacagagga gcagcggatg atgatcaggg agctgatgga cgctcagatg     780
aaaaccttg acactacctt ctcccatttc aagaatttcc ggctgccagg ggtgcttagc     840
agtggctgcg agttgccaga gtctctgcag gccccatcga gggaagaagc tgccaagtgg     900
agccaggtcc ggaaagatct gtgctctttg aaggtctctc tgcagctgcg ggggaggat     960
ggcagtgtct ggaactacaa accccccagcc gacagtggcg ggaaagagat cttctccctg    1020
ctgccccaca tggctgacat gtcaacctac atgttcaaag gcatcatcag ctttgccaaa    1080
gtcatctcct acttcaggga cttgcccatc gaggaccaga tctccctgct gaaggggggcc   1140
gctttcgagc tgtgtcaact gagattcaac acagtgttca acgcggagac tggaacctgg    1200
gagtgtggcc ggctgtccta ctgcttggaa gacactgcag gtggcttcca gcaacttcta    1260
ctggagccca tgctgaaatt ccactacatg ctgaagaagc tgcagctgca tgaggaggag    1320
tatgtgctga tgcaggccat ctccctcttc tccccagacc gcccaggtgt gctgcagcac    1380
cgcgtggtgg accagctgca ggagcaattc gccattactc tgaagtccta cattgaatgc    1440
aatcggcccc agcctgctca taggttcttg ttcctgaaga tcatggctat gctcaccgag    1500
ctccgcagca tcaatgctca gcacacccag cggctgctgc catccagga catacacccc    1560
tttgctacgc ccctcatgca ggagttgttc ggcatcacag gtagctgagc ggctgccctt    1620
gggtgacacc tccgagaggc agccagaccc agagccctct gagccgccac tcccgggcca    1680
agacagatgg acactgccaa gagccgacaa tgccctgctg gcctgtctcc ctagggaatt    1740
cctgctatga cagctggcta gcattcctca ggaaggacat gggtgccccc cacccccagt    1800
tcagtctgta gggagtgaag ccacagactc ttacgtggag agtgcactga cctgtaggtc    1860
aggaccatca gagaggcaag gttgcccttt ccttttaaaa ggccctgtgg tctggggaga    1920
aatccctcag atcccactaa agtgtcaagg tgtggaaggg accaagcgac caaggatagg    1980
ccatctgggg tctatgccca catacccacg tttgttcgct tcctgagtct tttcattgct    2040
acctctaata gtcctgtctc ccacttccca ctcgttcccc tcctcttccg agctgctttg    2100
tgggctccag gcctgtactc atcggcaggt gcatgagtat ctgtgg                   2146
```

<210> SEQ ID NO 14
<211> LENGTH: 434
<212> TYPE: PRT
<213> ORGANISM: Homo Sapien

```
<220> FEATURE:
<223> OTHER INFORMATION: Homo Sapien

<400> SEQUENCE: 14

Leu Glu Val Arg Pro Lys Glu Ser Trp Asn His Ala Asp Phe Val His
  1               5                  10                  15

Cys Glu Asp Thr Glu Ser Val Pro Gly Lys Pro Ser Val Asn Ala Asp
                 20                  25                  30

Glu Glu Val Gly Gly Pro Gln Ile Cys Arg Val Cys Gly Asp Lys Ala
             35                  40                  45

Thr Gly Tyr His Phe Asn Val Met Thr Cys Glu Gly Cys Lys Gly Phe
     50                  55                  60

Phe Arg Arg Ala Met Lys Arg Asn Ala Arg Leu Arg Cys Pro Phe Arg
 65              70                  75                  80

Lys Gly Ala Cys Glu Ile Thr Arg Lys Thr Arg Arg Gln Cys Gln Ala
                 85                  90                  95

Cys Arg Leu Arg Lys Cys Leu Glu Ser Gly Met Lys Lys Glu Met Ile
            100                 105                 110

Met Ser Asp Glu Ala Val Glu Glu Arg Arg Ala Leu Ile Lys Arg Lys
            115                 120                 125

Lys Ser Glu Arg Thr Gly Thr Gln Pro Leu Gly Val Gln Gly Leu Thr
            130                 135                 140

Glu Glu Gln Arg Met Met Ile Arg Glu Leu Met Asp Ala Gln Met Lys
145                 150                 155                 160

Thr Phe Asp Thr Thr Phe Ser His Phe Lys Asn Phe Arg Leu Pro Gly
                165                 170                 175

Val Leu Ser Ser Gly Cys Glu Leu Pro Glu Ser Leu Gln Ala Pro Ser
            180                 185                 190

Arg Glu Glu Ala Ala Lys Trp Ser Gln Val Arg Lys Asp Leu Cys Ser
            195                 200                 205

Leu Lys Val Ser Leu Gln Leu Arg Gly Glu Asp Gly Ser Val Trp Asn
            210                 215                 220

Tyr Lys Pro Pro Ala Asp Ser Gly Gly Lys Glu Ile Phe Ser Leu Leu
225                 230                 235                 240

Pro His Met Ala Asp Met Ser Thr Tyr Met Phe Lys Gly Ile Ile Ser
                245                 250                 255

Phe Ala Lys Val Ile Ser Tyr Phe Arg Asp Leu Pro Ile Glu Asp Gln
            260                 265                 270

Ile Ser Leu Leu Lys Gly Ala Ala Phe Glu Leu Cys Gln Leu Arg Phe
            275                 280                 285

Asn Thr Val Phe Asn Ala Glu Thr Gly Thr Trp Glu Cys Gly Arg Leu
            290                 295                 300

Ser Tyr Cys Leu Glu Asp Thr Ala Gly Gly Phe Gln Gln Leu Leu Leu
305                 310                 315                 320

Glu Pro Met Leu Lys Phe His Tyr Met Leu Lys Lys Leu Gln Leu His
                325                 330                 335

Glu Glu Glu Tyr Val Leu Met Gln Ala Ile Ser Leu Phe Ser Pro Asp
            340                 345                 350

Arg Pro Gly Val Leu Gln His Arg Val Val Asp Gln Leu Gln Glu Gln
            355                 360                 365

Phe Ala Ile Thr Leu Lys Ser Tyr Ile Glu Cys Asn Arg Pro Gln Pro
            370                 375                 380

Ala His Arg Phe Leu Phe Leu Lys Ile Met Ala Met Leu Thr Glu Leu
385                 390                 395                 400
```

-continued

```
Arg Ser Ile Asn Ala Gln His Thr Gln Arg Leu Leu Arg Ile Gln Asp
            405                 410                 415

Ile His Pro Phe Ala Thr Pro Leu Met Gln Glu Leu Phe Gly Ile Thr
            420                 425                 430

Gly Ser
```